United States Patent
Carlson et al.

(10) Patent No.: US 12,364,455 B2
(45) Date of Patent: Jul. 22, 2025

(54) REDUCING CATHETER ROTATION MOTOR PWM INTERFERENCE WITH INTRAVASCULAR ULTRASOUND IMAGING

(71) Applicant: Boston Scientific Scimed, Inc., Maple Grove, MN (US)

(72) Inventors: Corydon Carlson, Stillwater, MN (US); Wenguang Li, Los Gatos, CA (US); Anming He Cai, San Jose, CA (US); Michael William Hansen, Maple Grove, MN (US); Timothy G. Curran, St. Paul, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 253 days.

(21) Appl. No.: 18/101,979

(22) Filed: Jan. 26, 2023

(65) Prior Publication Data
US 2023/0233178 A1    Jul. 27, 2023

Related U.S. Application Data

(60) Provisional application No. 63/303,287, filed on Jan. 26, 2022.

(51) Int. Cl.
*A61B 8/12* (2006.01)
*A61B 8/00* (2006.01)

(52) U.S. Cl.
CPC .............. *A61B 8/12* (2013.01); *A61B 8/445* (2013.01); *A61B 8/4483* (2013.01)

(58) Field of Classification Search
CPC .......... A61B 8/12; A61B 8/445; A61B 8/4483
See application file for complete search history.

(56) References Cited

U.S. PATENT DOCUMENTS

| | | | |
|---|---|---|---|
| 5,509,418 A * | 4/1996 | Lum | A61B 8/4461 600/463 |
| 6,945,938 B2 | 9/2005 | Grunwald | |
| 7,246,959 B2 | 7/2007 | Nakatani | |
| 7,306,561 B2 | 12/2007 | Sathyanarayana | |
| 10,902,564 B2 | 1/2021 | Courtney et al. | |
| 2006/0100522 A1 | 5/2006 | Yuan et al. | |
| 2006/0106320 A1 | 5/2006 | Barbato | |
| 2006/0173350 A1 | 8/2006 | Yuan et al. | |
| 2006/0253028 A1 | 11/2006 | Lam et al. | |
| 2007/0016054 A1 | 1/2007 | Cao et al. | |
| 2007/0038111 A1 | 2/2007 | Rehrig et al. | |
| 2008/0285824 A1* | 11/2008 | Wildes | A61B 8/4245 382/128 |
| 2014/0187963 A1 | 7/2014 | Corl | |
| 2015/0073279 A1 | 3/2015 | Cai et al. | |
| 2017/0049298 A1* | 2/2017 | Hunter | A61B 5/067 |

OTHER PUBLICATIONS

International Search Report and Written Opinion dated Mar. 30, 2023 for International Application No. PCT/US2023/011641.

* cited by examiner

*Primary Examiner* — Sean A Frith
(74) *Attorney, Agent, or Firm* — Seager, Tufte & Wickhem, LLP

(57) ABSTRACT

Methods include capturing intravascular ultrasound images. A drive motor is used to actively drive an ultrasound transducer at a set rotation speed. A temporary sensing window is created in which the ultrasound transducer is driven with a fixed drive signal. A plurality of signals from are received the ultrasound transducer during the temporary sensing window.

19 Claims, 19 Drawing Sheets

REDUCING CATHETER ROTATION MOTOR PWM INTERFERENCE WITH INTRAVASCULAR ULTRASOUND IMAGING

CROSS-REFERENCE TO RELATED APPLICATIONS

This application claims the benefit of priority under 35 U.S.C. § 119 of U.S. Provisional Application No. 63/303,287, filed Jan. 26, 2022, the entire disclosure of which is hereby incorporated by reference.

TECHNICAL FIELD

The present disclosure pertains to intravascular ultrasound imaging.

BACKGROUND

A wide variety of medical devices have been developed for medical use, for example, intravascular use. Some of these devices include intravascular ultrasound imaging devices. In addition, methods for intravascular ultrasound imaging have been developed. Of these devices and methods, each has certain advantages and disadvantages. There is an ongoing need to provide alternative devices as well as alternative methods.

BRIEF SUMMARY

This disclosure provides design and use alternatives for medical devices as well as methods, for example methods that include intravascular ultrasound imaging. As an example, a method for capturing intravascular ultrasound images using a mechanically steered transducer is disclosed. The method includes generating a Pulse Width Modulation (PWM) drive signal and using the PWM drive signal to actuate a drive motor for an intravascular ultrasound catheter including an ultrasound transducer in order to rotate the ultrasound transducer at a set rotation speed. A sensing window in which the PWM drive signal is not being switched in order to reduce electrical noise is created and a plurality of signals are received from the ultrasound transducer during the sensing window.

Alternatively or additionally, the method may further include returning to allowing the PWM drive signal to be switched after the sensing window has terminated.

Alternatively or additionally, the method may further include altering the PWM drive signal in order to adjust a rotation speed of the ultrasound transducer relative to the set rotation speed just before a start of the sensing window.

Alternatively or additionally, altering the PWM drive signal in order to adjust a rotation speed of the ultrasound transducer may include altering the PWM drive signal in order to rotate the ultrasound transducer at an increased rotation speed greater than the set rotation speed just before the start of the sensing window.

Alternatively or additionally, the increased rotation speed may last for a first period of time terminating at the start of the sensing window.

Alternatively or additionally, the method may further include altering the PWM drive signal in order to adjust a rotation speed of the ultrasound transducer relative to the set rotation speed just after an end of the sensing window.

Alternatively or additionally, altering the PWM drive signal in order to adjust a rotation speed of the ultrasound transducer may include altering the PWM drive signal in order to rotate the ultrasound transducer at a decreased speed relative to the set rotation speed just after the end of the sensing window.

Alternatively or additionally, the method may further include altering the PWM drive signal in order to return to rotating the ultrasound transducer at the set rotation speed after a second period of time beginning at the end of the sensing window.

As another example, a method for capturing intravascular ultrasound images is disclosed. The method includes using a drive motor to actively drive an ultrasound transducer at a set rotation speed in accordance with a time-varying drive motor drive signal. A sensing window in which the drive motor drive signal is unswitched is created and a plurality of signals are received from the ultrasound transducer during the temporary sensing window.

Alternatively or additionally, the method may further include once again allowing the drive motor drive signal to be switched in order to drive the ultrasound transducer at the set rotation speed once the temporary sensing window has ended.

Alternatively or additionally, the method may further include temporarily increasing the rotation speed of the ultrasound transducer above the set rotation speed for a brief period of time before a start of the temporary sensing window.

Alternatively or additionally, the method may further include temporarily decreasing the rotation speed of the ultrasound transducer, below the set rotation speed, for a brief period of time immediately after an end of the temporary sensing window.

Alternatively or additionally, the method may further include increasing the rotation speed of the ultrasound transducer to equal the set rotation speed once the brief period of time has ended.

Alternatively or additionally, the drive motor may be controlled via a Pulse Width Modulation (PWM) drive signal.

Alternatively or additionally, a state of the drive motor drive signal during the temporary sensing window may be dynamically determined based on motor speed and/or load.

As another example, a method for capturing intravascular ultrasound images is disclosed. The method includes rotating an ultrasound transducer using a digital drive motor operating in accordance with a varying drive signal. The ultrasound transducer is rotated using the digital drive motor operating in accordance with an unchanging drive signal for a brief period of time and signals from the ultrasound transducer are sensed during the brief period of time.

Alternatively or additionally, sensing signals from the ultrasound transducer may further include not sensing signals form the ultrasound transducer when the digital drive motor is operating in accordance with the varying drive signal.

Alternatively or additionally, a state of the drive motor drive signal during the temporary sensing window may be dynamically determined based on motor speed and/or load.

Alternatively or additionally, the method may further include using a Pulse Width Modulation (PWM) drive signal to control the digital drive motor.

Alternatively or additionally, the method may further include altering a rotation speed of the ultrasound transducer either just before or just after the brief period of time.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
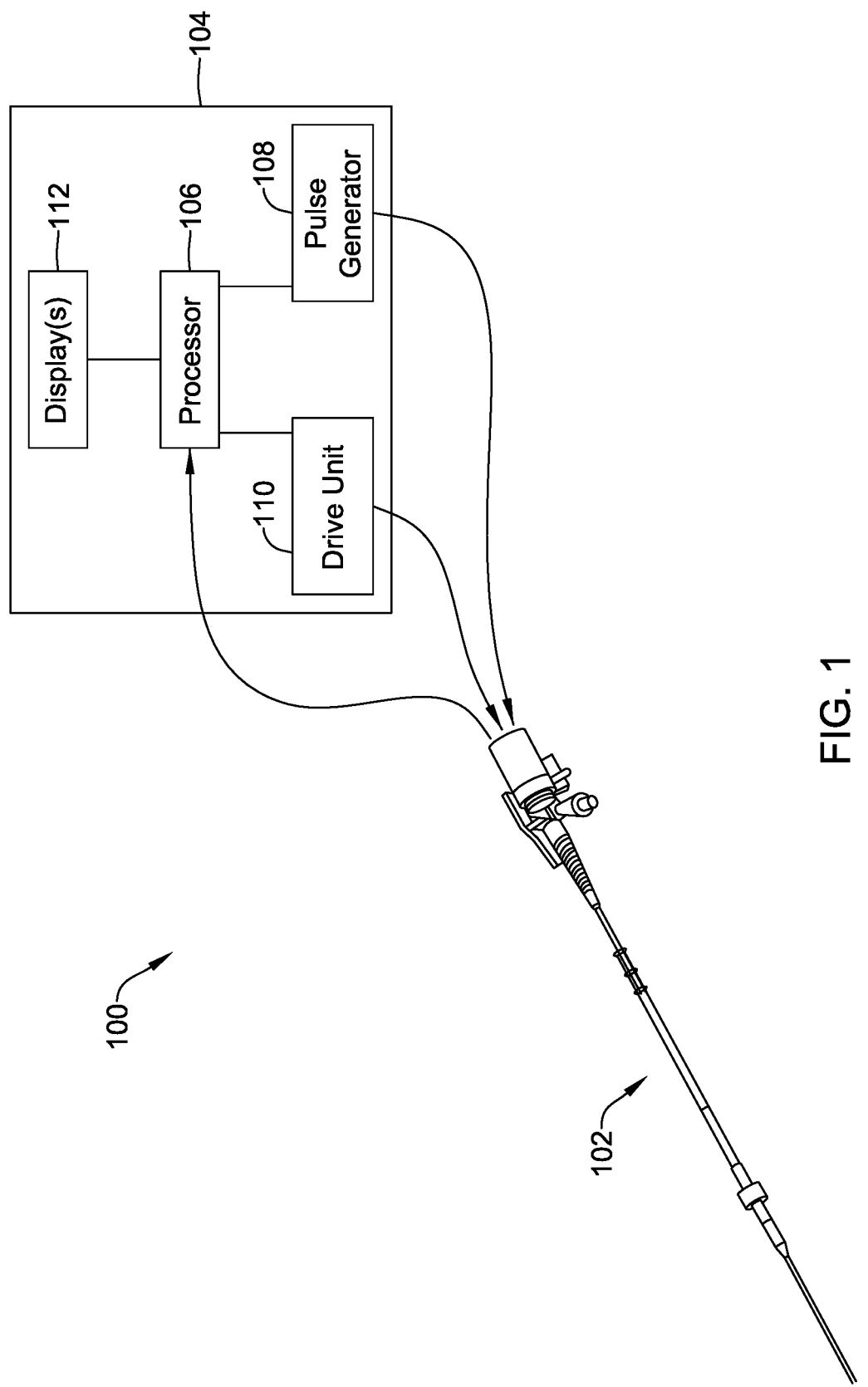
FIG. 1 is a schematic view of an illustrative intravascular ultrasound system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Ultrasound devices insertable into patients have proven diagnostic capabilities for a variety of diseases and disorders. For example, intravascular ultrasound ("IVUS") imaging systems may be used as an imaging modality for diagnosing blocked blood vessels and providing information to aid medical practitioners in selecting and placing stents and other devices to restore or increase blood flow. IVUS imaging systems may also be used to diagnose atheromatous plaque build-up at particular locations within blood vessels. IVUS imaging systems may also be used to determine the existence of an intravascular obstruction or stenosis, as well as the nature and degree of the obstruction or stenosis. IVUS imaging systems may also be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems may also be used to monitor or assess ongoing intravascular treatments, such as angiography and stent placement in real (or almost real) time. Moreover, IVUS imaging systems may be used to monitor one or more heart chambers.

IVUS imaging systems have been developed to provide a diagnostic tool for visualizing a variety of diseases or disorders. An IVUS imaging system may include a control module (with a pulse generator, an image processor, and a monitor), a catheter, and one or more transducers disposed in the catheter. The transducer-containing catheter may be positioned in a lumen or cavity within, or in proximity to, a region to be imaged, such as a blood vessel wall or patient tissue in proximity to a blood vessel wall. The pulse generator in the control module may generate electrical pulses that are delivered to the one or more transducers and transformed to acoustic pulses that are transmitted through patient tissue. Reflected pulses of the transmitted acoustic pulses may be absorbed by the one or more transducers and transformed to electric pulses. The transformed electric pulses may be delivered to the image processor and converted to an image displayable on the monitor.

FIG. 1 illustrates schematically an illustrative IVUS imaging system 100. The IVUS imaging system 100 includes a catheter 102 that is couplable to a processing unit or control module 104. The control module 104 may include, for example, a processor 106, a pulse generator 108, a drive unit 110, and one or more displays 112. In some instances, the pulse generator 108 forms electric pulses that may be input to one or more transducers (312 in FIG. 3) disposed in the catheter 102.

In some instances, mechanical energy from the drive unit 110 may be used to drive an imaging core (306 in FIG. 3) disposed in the catheter 102. In some instances, electric signals transmitted from the one or more transducers (312 in FIG. 3) may be input to the processor 106 for processing. In some instances, the processed electric signals from the one or more transducers (312 in Figure) can be displayed as one or more images on the one or more displays 112. For example, a scan converter can be used to map scan line samples (e.g., radial scan line samples, or the like) to a two-dimensional Cartesian grid to display the one or more images on the one or more displays 112.

In some instances, the processor 106 may also be used to control the functioning of one or more of the other components of the control module 104. For example, the processor 106 may be used to control at least one of the frequency or duration of the electrical pulses transmitted from the pulse generator 108, the rotation rate of the imaging core (306 in Figure) by the drive unit 110, the velocity or length of the pullback of the imaging core (306 in FIG. 3) by the drive unit 110, or one or more properties of one or more images formed on the one or more displays 112. In some instances, the processor 106 may also control operation of the drive unit 110. In some instances, the drive unit 110 may include a digital drive motor that is adapted to drive the catheter 102 or portions thereof, such as one or more ultrasound transducers (312 in FIG. 3) into rotation.

In some cases, the processor 106 may control the digital drive motor via a pulse width modulation (PWM) drive signal. A PWM drive signal may vary between on (or high) and off (or low). The PWM drive signal may regulate operation of the digital drive motor by adjusting how frequently the PWM drive signal is on (or high) and how frequently the PWM drive signal is off (or low). In some cases, the PWM drive signal may include a single signal or multiple signals. In some cases, the PWM drive signal may include a signal that is tri-state, rather than simply being on (or high) or off (or low).

Figure 2:
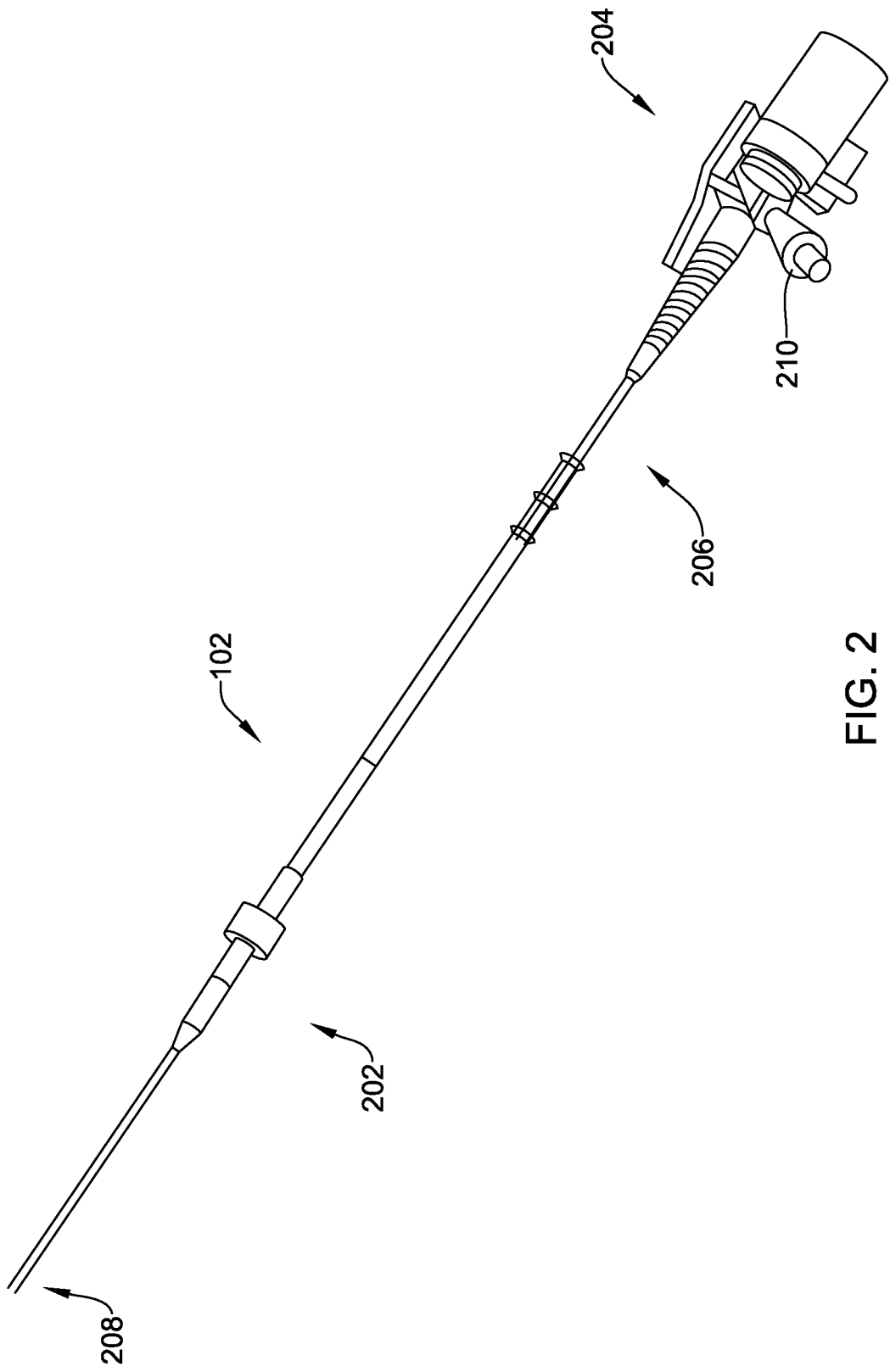
FIG. 2 is a perspective view of an illustrative intravascular ultrasound catheter system.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. Optionally, the catheter 102 may define at least one flush port, such as flush port 210. The flush port 210 may be defined in the hub 204. The hub 204 may be configured and arranged to couple to the control module (104 in FIG. 1). In some instances, the elongated member 202 and the hub 204 are formed as a unitary body. In other instances, the elongated member 202 and the catheter hub 204 are formed separately and subsequently assembled together.

Figure 3:
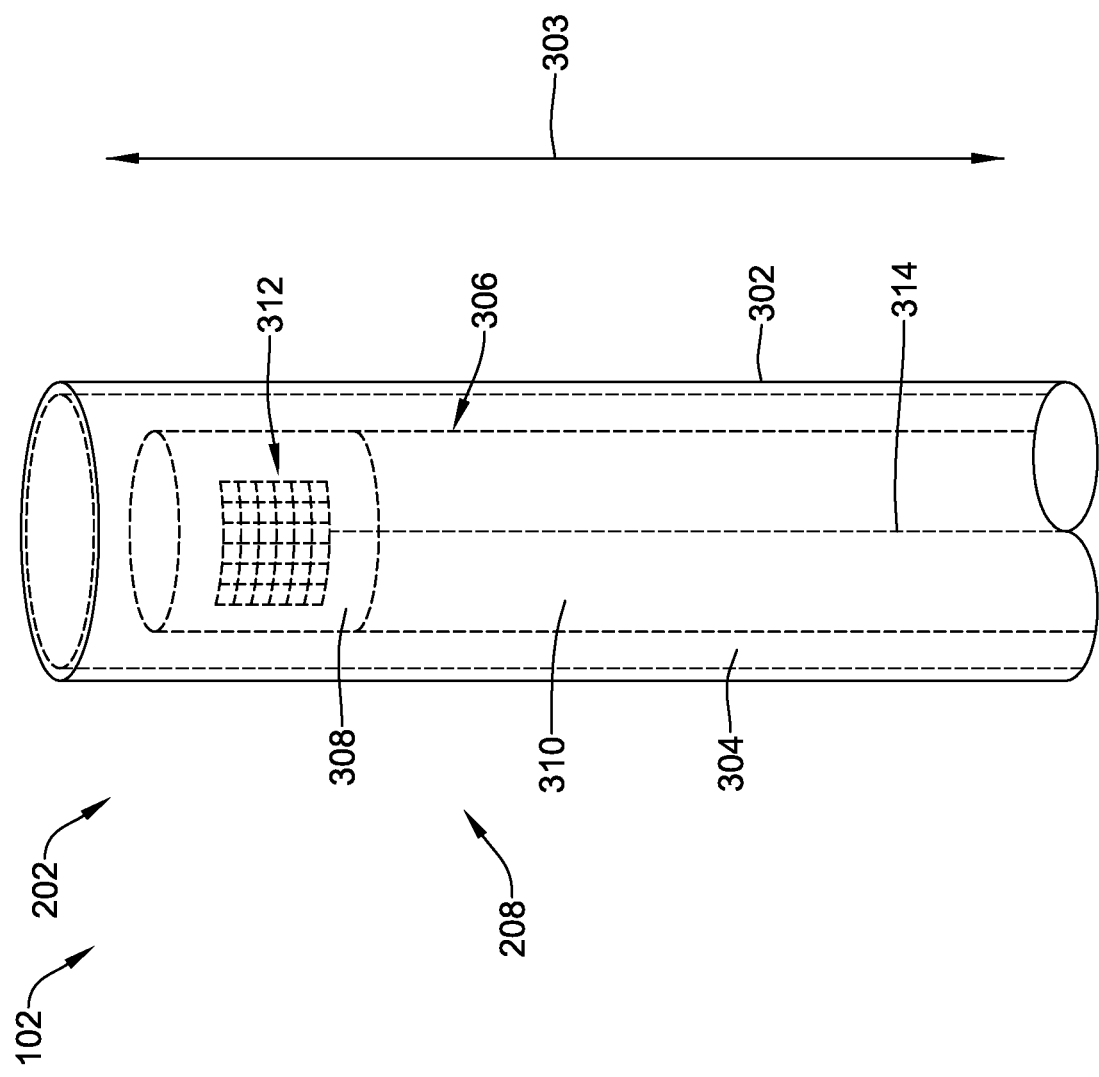
FIG. 3 is a side view of a portion of an illustrative intravascular ultrasound catheter system.

FIG. 3 is a schematic perspective view of one embodiment of the distal end 208 of the elongated member 202 of the catheter 102. The elongated member 202 includes a sheath 302 with a longitudinal axis 303 and a lumen 304. An imaging core 306 is disposed in the lumen 304. The imaging core 306 includes an imaging device 308 coupled to a distal end of a driveshaft 310 that is rotatable either manually or using a computer-controlled drive mechanism. One or more transducers 312 may be mounted to the imaging device 308 and employed to transmit and receive acoustic signals. The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

In some instances, for example as shown in FIG. 3, an array of transducers 312 are mounted to the imaging device 308. Alternatively, a single transducer may be employed. Any suitable number of transducers 312 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used. When a plurality of transducers 312 are employed, the transducers 312 can be configured into any suitable arrangement including, for example, an annular arrangement, a rectangular arrangement, or the like.

The one or more transducers 312 may be formed from materials capable of transforming applied electrical pulses to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like. Other transducer technologies include composite materials, single-crystal composites, and semiconductor devices (e.g., capacitive micromachined ultrasound transducers ("cMUT"), piezoelectric micromachined ultrasound transducers ("pMUT"), or the like).

The pressure distortions on the surface of the one or more transducers 312 form acoustic pulses of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic pulses of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a matching layer and a conductive backing material formed from an acoustically absorbent material (e.g., an epoxy substrate with tungsten particles). During operation, the piezoelectric layer may be electrically excited to cause the emission of acoustic pulses.

The one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

The imaging core 306 is rotated about the longitudinal axis 303 of the catheter 102. As the imaging core 306 rotates, the one or more transducers 312 emit acoustic signals in different radial directions (e.g., along different radial scan lines). For example, the one or more transducers 312 can emit acoustic signals at regular (or irregular) increments, such as 256 radial scan lines per revolution, or the like. It will be understood that other numbers of radial scan lines can be emitted per revolution, instead.

When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic pulses transmitted and the echo pulses received. In some instances, the rotation of the imaging core 306 is driven by the drive unit 110 disposed in the control module (104 in FIG. 1). In alternate embodiments, the one or more transducers 312 are fixed in place and do not rotate. In which case, the driveshaft 310 may, instead, rotate a mirror that reflects acoustic signals to and from the fixed one or more transducers 312.

When the one or more transducers 312 are rotated about the longitudinal axis 303 of the catheter 102 emitting acoustic pulses, a plurality of images can be formed that collectively form a radial cross-sectional image (e.g., a tomographic image) of a portion of the region surrounding the one or more transducers 312, such as the walls of a blood vessel of interest and tissue surrounding the blood vessel. The radial cross-sectional image can, optionally, be displayed on one or more displays 112. The at least one of the imaging core 306 can be either manually rotated or rotated using a computer-controlled mechanism.

The imaging core 306 may also move longitudinally along the blood vessel within which the catheter 102 is inserted so that a plurality of cross-sectional images may be formed along a longitudinal length of the blood vessel. During an imaging procedure the one or more transducers 312 may be retracted (e.g., pulled back) along the longitudinal length of the catheter 102. The catheter 102 can include at least one telescoping section that can be retracted during pullback of the one or more transducers 312. In some instances, the drive unit 110 drives the pullback of the imaging core 306 within the catheter 102. The drive unit 110 pullback distance of the imaging core can be any suitable distance including, for example, at least 5 cm, 10 cm, 15 cm, 20 cm, 25 cm, or more. The entire catheter 102 can be retracted during an imaging procedure either with or without the imaging core 306 moving longitudinally independently of the catheter 102.

A motor may, optionally, be used to pull back the imaging core 306. The motor can pull back the imaging core 306 a short distance and stop long enough for the one or more transducers 306 to capture an image or series of images before pulling back the imaging core 306 another short distance and again capturing another image or series of images, and so on.

The quality of an image produced at different depths from the one or more transducers 312 may be affected by one or more factors including, for example, bandwidth, transducer focus, beam pattern, as well as the frequency of the acoustic pulse. The frequency of the acoustic pulse output from the one or more transducers 312 may also affect the penetration depth of the acoustic pulse output from the one or more transducers 312. In general, as the frequency of an acoustic pulse is lowered, the depth of the penetration of the acoustic pulse within patient tissue increases. In some instances, the IVUS imaging system 100 operates within a frequency range of 5 MHz to 100 MHz.

One or more conductors 314 can electrically couple the transducers 312 to the control module 104 (see, for example, FIG. 1). In which case, the one or more conductors 314 may extend along a longitudinal length of the rotatable driveshaft 310.

The catheter 102 with one or more transducers 312 mounted to the distal end 208 of the imaging core 308 may be inserted percutaneously into a patient via an accessible blood vessel, such as the femoral artery, femoral vein, or jugular vein, at a site remote from the selected portion of the selected region, such as a blood vessel, to be imaged. The catheter 102 may then be advanced through the blood vessels of the patient to the selected imaging site, such as a portion of a selected blood vessel.

An image or image frame ("frame") can be generated each time one or more acoustic signals are output to surrounding tissue and one or more corresponding echo signals are received by the imager 308 and transmitted to the processor 106. Alternatively, an image or image frame can be a composite of scan lines from a full or partial rotation of the imaging core or device. A plurality (e.g., a sequence) of frames may be acquired over time during any type of movement of the imaging device 308. For example, the frames can be acquired during rotation and pullback of the imaging device 308 along the target imaging location. It will be understood that frames may be acquired both with or without rotation and with or without pullback of the imaging device 308. Moreover, it will be understood that frames may be acquired using other types of movement procedures in addition to, or in lieu of, at least one of rotation or pullback of the imaging device 308.

In some instances, when pullback is performed, the pullback may be at a constant rate, thus providing a tool for potential applications able to compute longitudinal vessel/plaque measurements. In some instances, the imaging device 308 is pulled back at a constant rate of at least 0.3 mm/s. In some instances, the imaging device 308 is pulled back at a constant rate of at least 0.4 mm/s. In some instances, the imaging device 308 is pulled back at a constant rate of at least 0.5 mm/s. In some instances, the imaging device 308 is pulled back at a constant rate of at least 0.6 mm/s. In some instances, the imaging device 308 is pulled back at a constant rate of at least 0.7 mm/s. In some instances the imaging device 308 is pulled back at a constant rate of at least 0.8 mm/s.

In some instances, the one or more acoustic signals are output to surrounding tissue at constant intervals of time. In some instances, the one or more corresponding echo signals are received by the imager 308 and transmitted to the processor 106 at constant intervals of time. In some instances, the resulting frames are generated at constant intervals of time.

At least some conventional IVUS imaging systems display only a single (e.g., cross-sectional, longitudinal, or the like) image during, or after, an IVUS procedure, such as a pull-back procedure. It may, however, be useful to concurrently display, in real-time during the IVUS procedure (e.g., a pull-back procedure), at least two images, such as the most recently processed image and a previously-obtained image that has some particular or selected image characteristic (e.g., maximum or minimum lumen area or diameter).

Figure 4:
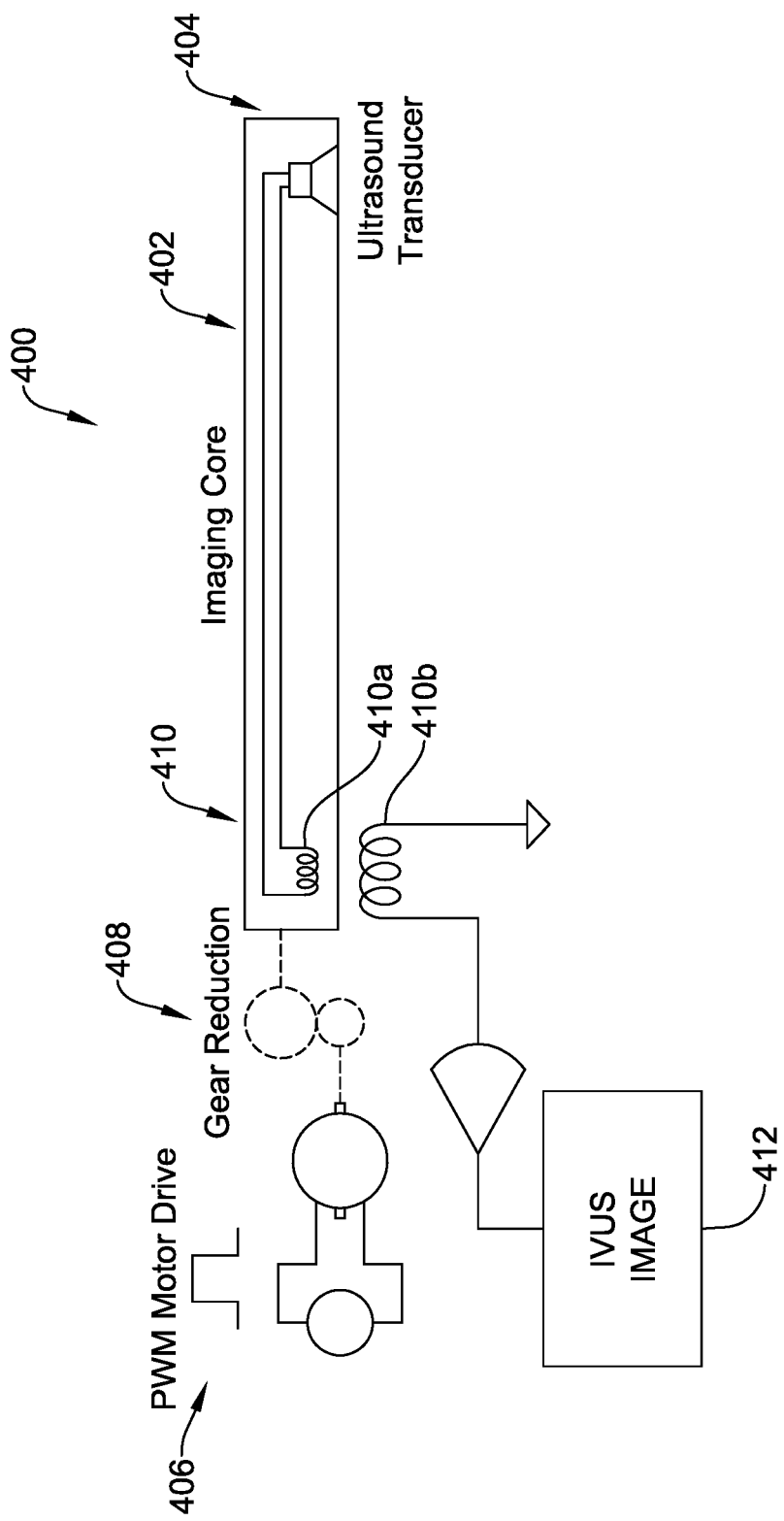
FIG. 4 is a schematic view of an illustrative intravascular ultrasound system.

FIG. 4 is a schematic view of an illustrative IVUS imaging system 400. The IVUS imaging system 400 may be considered as being an example of the illustrative IVUS imaging system 100 shown in FIG. 1. Various features described herein as part of the IVUS imaging system 100 may similarly be considered as being part of the IVUS imaging system 400. Similarly, various features described herein as part of the IVUS imaging system 400 may also be considered as being part of the IVUS imaging system 100.

The IVUS imaging system 400 includes an imaging core 402, which may be considered as being an example of the catheter 102 shown in FIG. 1. The imaging core 402 includes an ultrasound transducer 404, which may be considered as being an example of the ultrasound transducer 312 shown in FIG. 3. While a single ultrasound transducer 404 is shown, it will be appreciated that the imaging core 402 may have any number of ultrasound transducers 404.

The imaging core 402, and thus the ultrasound transducer 404, may be driven into rotation via a drive motor 406 that is operably coupled to the imaging core 402 via a gear reduction mechanism 408. The drive motor 406 may be a brushless digital motor, for example, although in some cases a brushed motor is contemplated. The drive motor 406 may be operated in accordance with a PWM drive signal. In some cases, the PWM drive signal may be generated by the processor 106 shown in FIG. 1. A PWM drive signal is a digital signal that is either high (on) or low (off), and has a value that is either one (1) or zero (0). The operating speed of the drive motor 406 may vary in accordance with how often the PWM drive signal is high (on, or set equal to one) and how often the PWM drive signal is low (off, or set equal to zero).

The gear reduction mechanism 408 may provide a speed reduction for the imaging core 402 relative to a rotational speed of the drive motor 406. For example, the gear reduction mechanism 408 may provide a 4 to 1 speed reduction or a 5 to 1 speed reduction. In some cases, the gear reduction mechanism 408 may provide a speed reduction that is about a 4.5 to 1 speed reduction. As an illustration, the drive motor 406 may rotate at 5000 to 6000 revolutions per minute (RPM) while the imaging core 402 may rotate at a reduced speed in the range of about 1800 RPM. This rotation speed corresponds to the ultrasound transducer being able to capture 30 frames per second. These are just examples.

A transformer 410 provides for an electrical coupling with the imaging core 402. The transformer 410 includes a first winding 410a that is coupled with the imaging core 402, and thus rotates, and a second winding 410b that is stationary. An electric field generated by the moving first winding 410a can be picked up via the second winding 410b. As a result, signals from the ultrasound transducer 404 can be transmitted from the imaging core 402 to an IVUS image 412. It will be appreciated that the signals from the ultrasound transducer 404 may undergo a variety of processing before being displayed as the IVUS image 412.

In some cases, as noted, a PWM drive signal may be used for controlling operation of the drive motor 406. Using a PWM drive signal provides advantages such as but not limited to fewer components, meaning that using a PWM drive can result in cost savings, less power consumed and more reliable. Using a PWM drive can mean faster responses to command changes. In some cases, using a PWM drive signal can produce noise in the corresponding IVUS images. Because a PWM drive signal alternates between high and low, every time the PWM drive signal switches a variety of electrical noise can be produced, and this noise can manifest itself as speckles on an IVUS image. Speckles are undesired image components that are created by detection circuits detecting electrical noise rather than actual (real or expected) data from the ultrasound transducer.

Figure 5B:
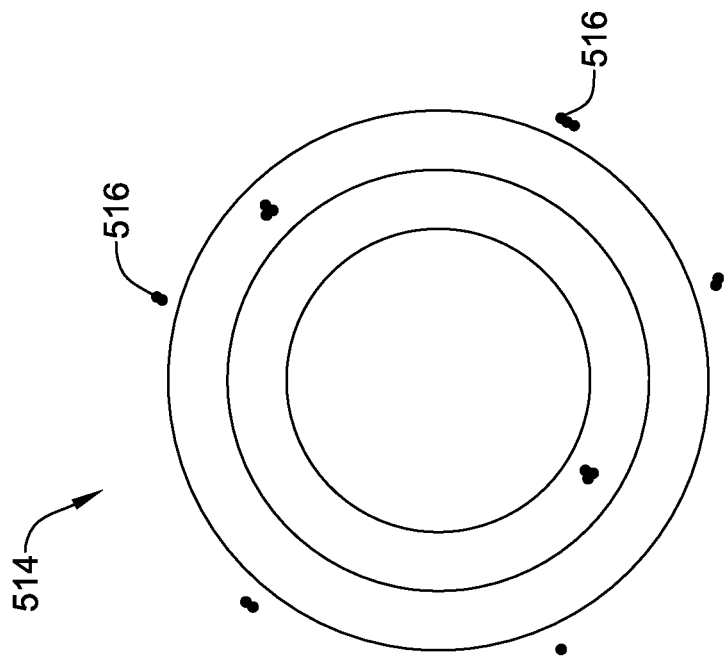
FIG. 5B is an illustrative ultrasound image that includes artifacts caused by motor noise.
Figure 5A:
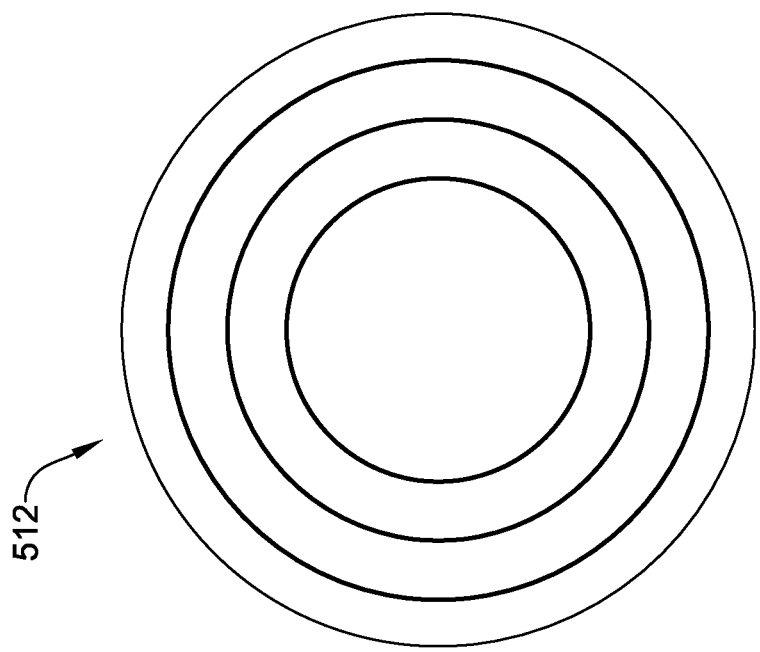
FIG. 5A is an illustrative ultrasound image that does not include artifacts caused by motor noise.

FIG. 5A shows a first IVUS image 512 that is free of speckles while FIG. 5B shows a second IVUS image 514 that is similar to the first IVUS image 512, but includes a plurality of speckles. These speckles, and any other visible manifestation of electrical noise, can result in difficulties in obtaining clear IVUS images and properly interpreting the IVUS images with respect to the anatomy being represented in those IVUS images. FIGS. 6 through 13 are flow diagrams showing illustrative methods of capturing ultrasound images in a manner that reduces or even eliminates any visual manifestations of electrical noise that can be caused by the PWM drive signal switching between high (or on) and low (or off) while capturing intravascular ultrasound images.

Figure 6:
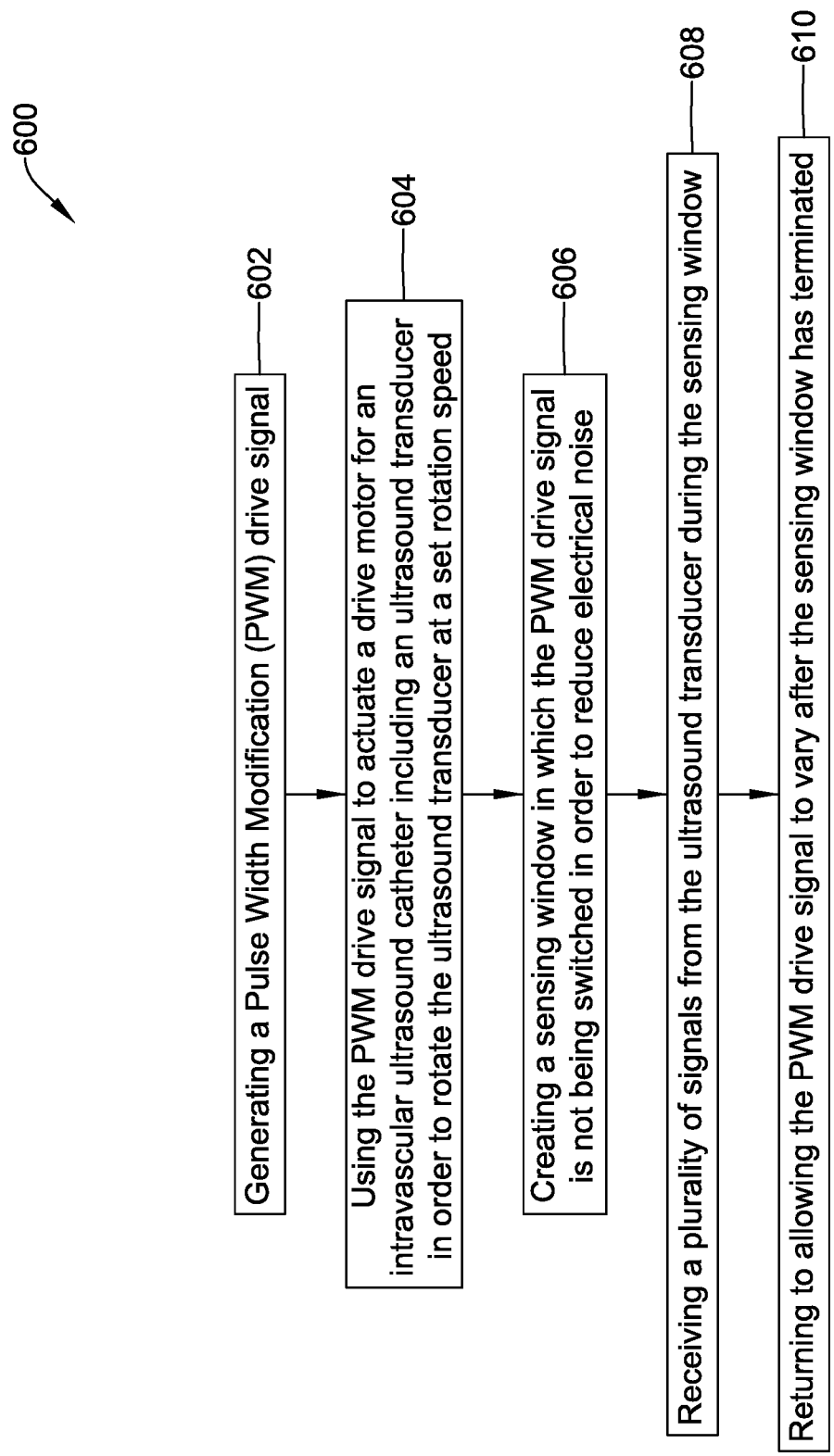
FIG. 6 is a flow diagram showing an illustrative method of capturing intravascular ultrasound images.

FIG. 6 is a flow diagram showing an illustrative method 600 for capturing intravascular ultrasound images using a mechanically steered transducer. The method 600 includes generating a Pulse Width Modulation (PWM) drive signal, as indicated at block 602. The PWM drive signal is used to actuate a drive motor (such as the drive motor 406) for an intravascular ultrasound catheter (such as the catheter 102 shown in FIGS. 1-3 or the imaging core 402 shown in FIG. 4) that includes an ultrasound transducer (such as the ultrasound transducer 312 or the ultrasound transducer 404) in order to rotate the ultrasound transducer at a set rotation speed, as indicated at block 604. The set rotation speed may be set or adjusted by an operator, for example, or may be a factory setting. The set rotation speed represents a target operating speed.

A sensing window in which the PWM drive signal is temporarily unswitched is created, as indicated at block 606 in order to reduce electrical noise. Holding the PWM drive signal steady may mean that the PWM drive signal is high, or on, meaning that the rotation speed may exceed the set rotation speed during the sensing window. Holding the PWM drive signal steady may mean that the PWM drive signal is low, or off, meaning that the rotation speed may decrease below the set rotation speed during the sensing window. In some cases, determining a state of the PWM drive signal during the sensing window may be dynamically determined based on motor speed and/or load just before the sensing window. If the motor speed is below a desired speed just before the sensing window, the PWM drive signal during the sensing window may be set to high, or on. If the motor speed is above a desired speed just before the sensing window, the PWM drive signal during the sensing window may be set to low, or off.

The sensing window may last for a short period of time, and may occur periodically. For example, in some cases, a sensing window may last from 0.1 percent to 0.5 percent of the time for an imaging core to make a full revolution. Motor speeds can range from 1000 to 2000 RPM. Accordingly, a sensing window may have a duration that ranges from 30 microseconds to over 200 microseconds, and a frequency that ranges from 4 kHz to 33 kHz.

A plurality of signals may be received from the ultrasound transducer during the sensing window, as indicated at block 608. In some cases, once the sensing window has ended, the PWM drive signal returns to being a time-varying signal, as indicated at block 610. It will be appreciated that the sensing window may be created periodically by not allowing the PWM drive signal to switch for a period of time corresponding to the sensing window, with intervening time periods of allowing the PWM drive signal to switch between high and low in order to maintain a desired rotation speed.

Figure 7:
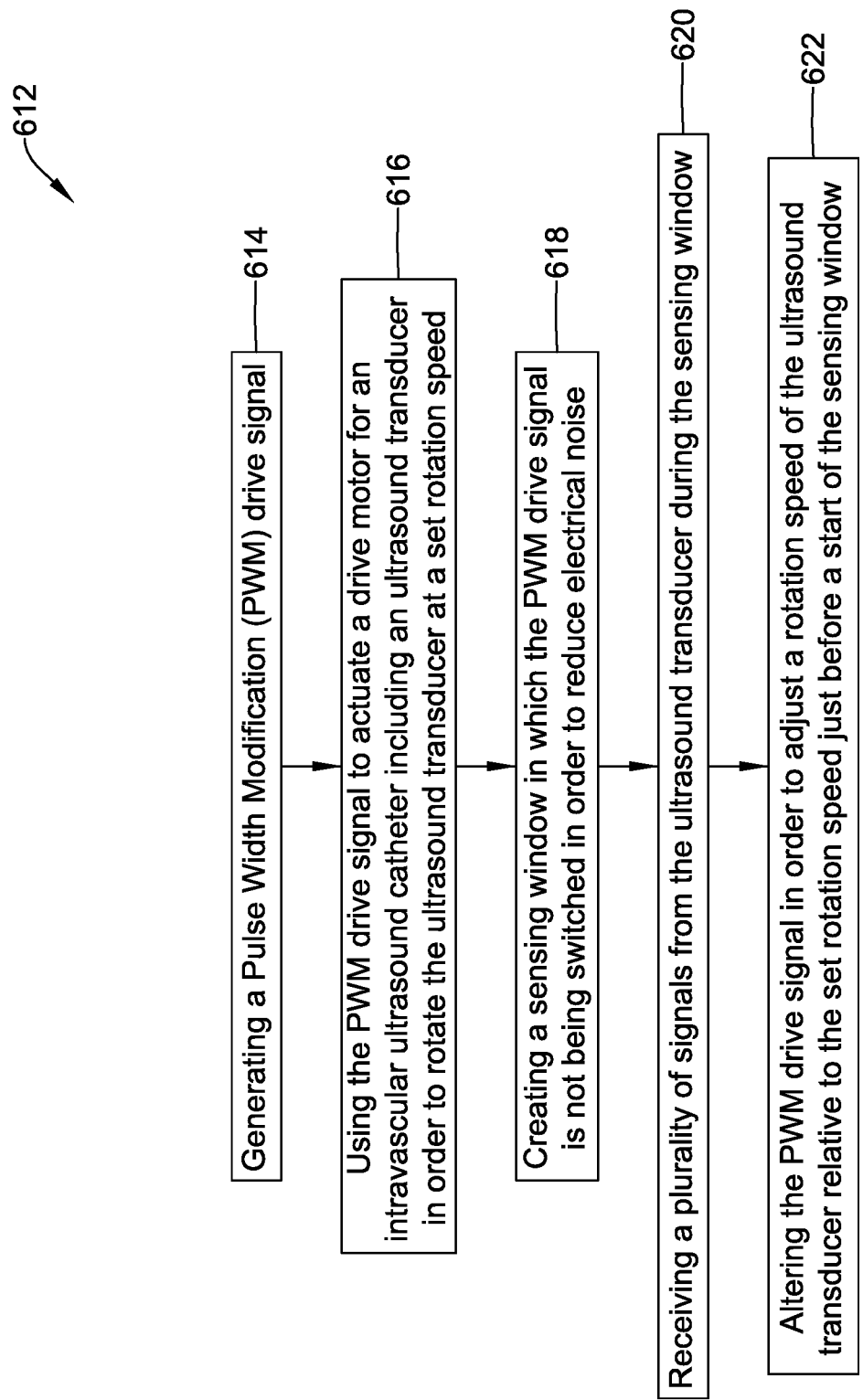
FIG. 7 is a flow diagram showing an illustrative method of capturing intravascular ultrasound images.

FIG. 7 is a flow diagram showing an illustrative method 612 for capturing intravascular ultrasound images. The method 612 includes generating a Pulse Width Modulation (PWM) drive signal, as indicated at block 614. The PWM drive signal is used to actuate a drive motor (such as the drive motor 406) for an intravascular ultrasound catheter (such as the catheter 102 shown in FIGS. 1-3 or the imaging core 402 shown in FIG. 4) that includes an ultrasound transducer (such as the ultrasound transducer 312 or the ultrasound transducer 404) in order to rotate the ultrasound transducer at a set rotation speed, as indicated at block 616. The set rotation speed may be set or adjusted by an operator, for example, or may be a factory setting. The set rotation speed represents a target operating speed.

A sensing window in which the PWM drive signal is temporarily held steady is created, as indicated at block 618. Holding the PWM drive signal steady may mean that the PWM drive signal is high, or on, meaning that the rotation speed may exceed the set rotation speed during the sensing window. Holding the PWM drive signal steady may mean that the PWM drive signal is low, or off, meaning that the rotation speed may decrease below the set rotation speed during the sensing window. The sensing window may last for a short period of time, and may occur periodically. For example, in some cases, a sensing window may last from 0.1 percent to 0.5 percent of the time for an imaging core to make a full revolution. Motor speeds can range from 1000 to 2000 RPM. Accordingly, a sensing window may have a duration that ranges from 30 microseconds to over 200 microseconds, and a frequency that ranges from 4 kHz to 33 kHz. A plurality of signals may be received from the ultrasound transducer during the sensing window, as indicated at block 620.

In some cases, the method 612 further includes altering the PWM drive signal in order to adjust a rotation speed of the ultrasound transducer relative to the set rotation speed just before a start of the sensing window, as indicated at block 622. In some instances, this may include altering the PWM drive signal in order to rotate the ultrasound transducer at an increased rotation speed greater than the set rotation speed just before the start of the sensing window. Depending on the duration of a particular sensing window, and the size and other characteristics of the ultrasound catheter, if the sensing window means that the PWM drive signal is constrained to low, or off, the ultrasound catheter may slow down too much during the sensing window when the drive motor is essentially coasting. Thus, speeding it up a little just before the sensing window can help to maintain the rotation speed of the ultrasound catheter and/or the ultrasound transducer. The increased rotation speed may last for a first period of time that terminates at the start of the sensing window. The first period of time may have a duration that ranges from near zero up to the entire time period between sampling windows. The time period may vary dynamically, depending on motor speed and load.

In some instances, altering the PWM drive signal just before a start of the sensing window may include adjusting the PWM drive signal in order to rotate the ultrasound transducer at a reduced rotation speed lower than the set rotation speed just before the start of the sensing window. There may be a desire to decrease the rotation speed just before the start of the sensing window if the PWM drive signal will be constrained to high, or on during the sensing window because the rotation speed of the ultrasound transducer will increase during the sensing window when the PWM drive signal is constrained to high, or on. In some cases, whether the PWM drive signal is altered just before the start of a sensing window may vary in order to accommodate a particular pattern in the PWM drive signal, for example.

Figure 8:
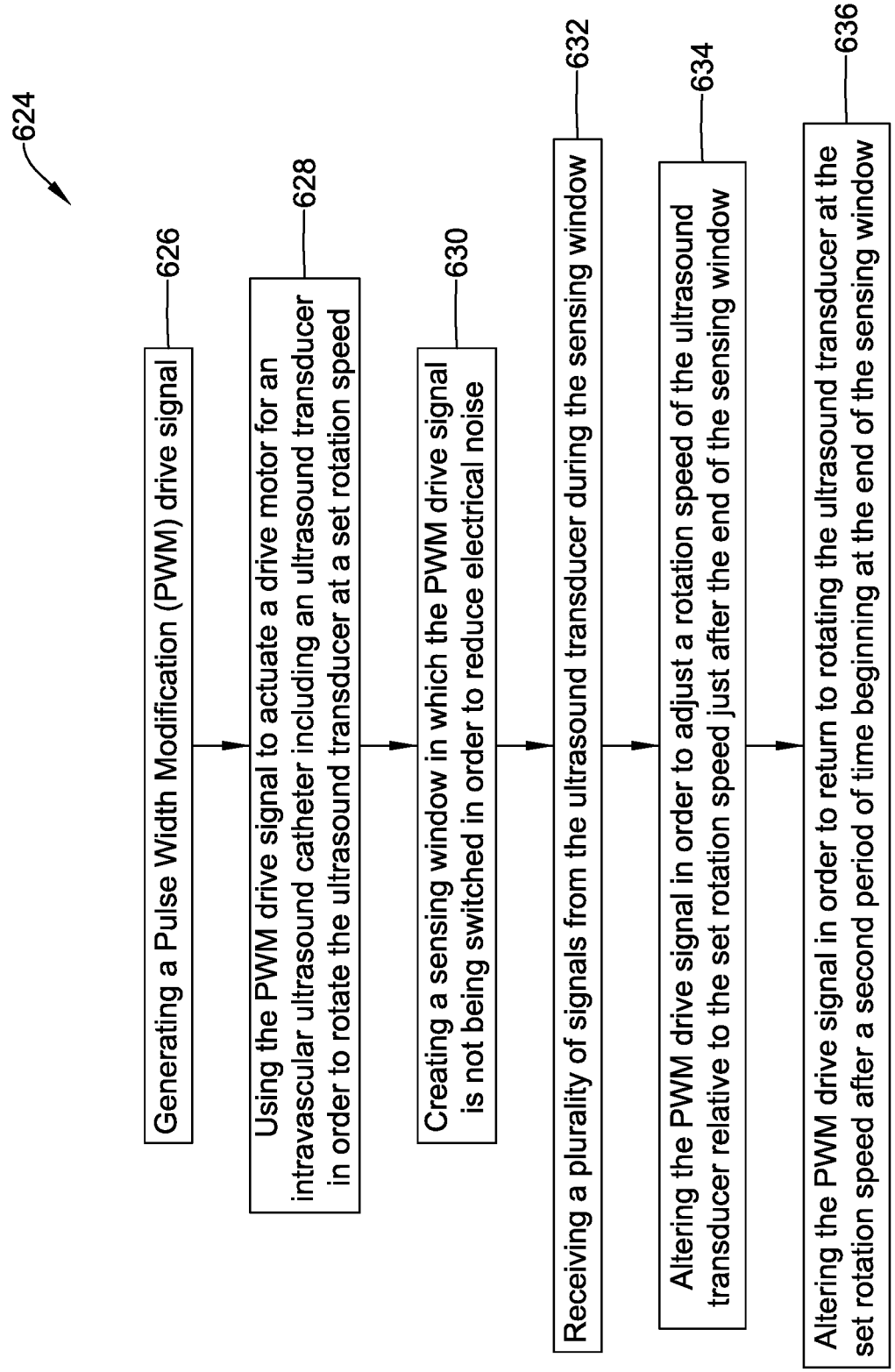
FIG. 8 is a flow diagram showing an illustrative method of capturing intravascular ultrasound images.

FIG. 8 is a flow diagram showing an illustrative method 624 for capturing intravascular ultrasound images. The method 624 includes generating a Pulse Width Modulation (PWM) drive signal, as indicated at block 626. The PWM drive signal is used to actuate a drive motor (such as the drive motor 406) for an intravascular ultrasound catheter (such as the catheter 102 shown in FIGS. 1-3 or the imaging core 402 shown in FIG. 4) that includes an ultrasound transducer (such as the ultrasound transducer 312 or the ultrasound transducer 404) in order to rotate the ultrasound transducer at a set rotation speed, as indicated at block 628. The set rotation speed may be set or adjusted by an operator, for example, or may be a factory setting. The set rotation speed represents a target operating speed.

A sensing window in which the PWM drive signal is temporarily held steady is created, as indicated at block 630. Holding the PWM drive signal steady may mean that the PWM drive signal is high, or on, meaning that the rotation speed may exceed the set rotation speed during the sensing window. Holding the PWM drive signal steady may mean that the PWM drive signal is low, or off, meaning that the rotation speed may decrease below the set rotation speed during the sensing window. The sensing window may last for a short period of time, and may occur periodically. For example, in some cases, a sensing window may last from 0.1 percent to 0.5 percent of the time for an imaging core to make a full revolution. Motor speeds can range from 1000 to 2000 RPM. Accordingly, a sensing window may have a duration that ranges from 30 microseconds to over 200 microseconds, and a frequency that ranges from 4 kHz to 33 kHz. A plurality of signals may be received from the ultrasound transducer during the sensing window, as indicated at block 632.

In some cases, the method 624 further includes altering the PWM drive signal in order to adjust a rotation speed of the ultrasound transducer relative to the set rotation speed just after an end of the sensing window, as indicated at block 634. In some cases, this includes altering the PWM drive signal in order to rotate the ultrasound transducer at a decreased speed relative to the set rotation speed just after the end of the sensing window. In some cases, using a decreased speed just after the end of the sensing window can reduce shocks applied to the ultrasound transducer. In some cases, altering the PWM drive signal may include altering the PWM drive signal in order to rotate the ultrasound transducer at an increased speed relative to the set rotation speed just after the end of the sensing window. In some cases, and as shown at block 636, the method 624 may further include altering the PWM drive signal in order to return to rotating the ultrasound transducer at the set rotation speed after a second period of time beginning at the end of the sensing window. The second period of time may have duration that ranges from 30 microseconds to over 200 microseconds.

Figure 9:
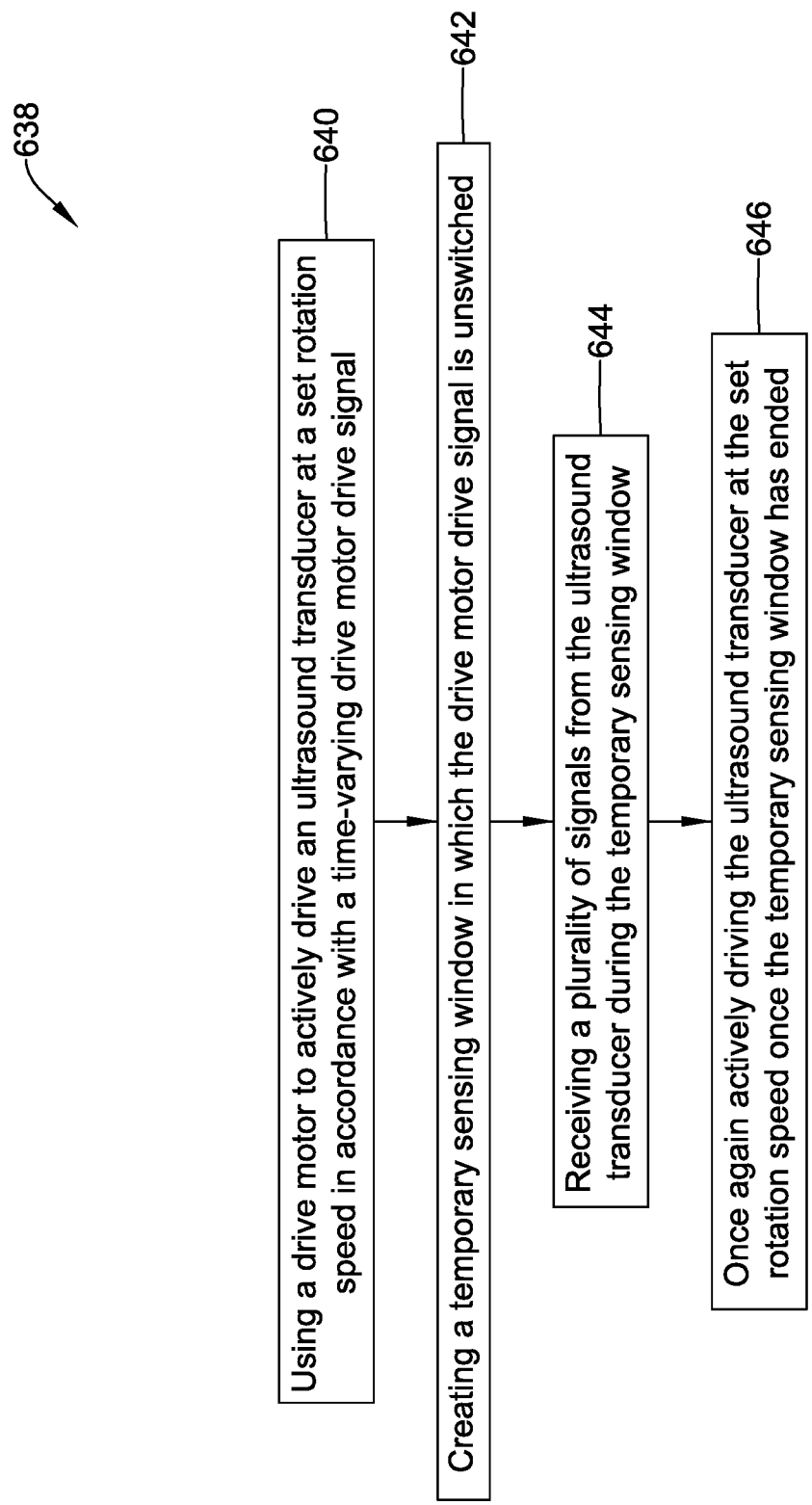
FIG. 9 is a flow diagram showing an illustrative method of capturing intravascular ultrasound images.

FIG. 9 is a flow diagram showing an illustrative method 638 for capturing intravascular ultrasound images. The method 638 includes using a drive motor (such as the drive motor 406) to actively drive an ultrasound transducer (such as the ultrasound transducer 312 or the ultrasound transducer 404) at a set rotation speed in accordance with a time-varying drive motor drive signal, as indicated at block 640. In some cases, the time-varying drive motor signal may include a PWM drive motor signal, for example. The set rotation speed may be set or adjusted by an operator, for example, or may be a factory setting. The set rotation speed represents a target operating speed.

A temporary sensing window is created in which the drive motor drive signal is held constant, i.e., not allowed to vary or switch, as indicated at block 642. The method 638 includes receiving a plurality of signals from the ultrasound transducer during the temporary sensing window, as indicated at block 644. In some cases, the method 638 may include once again actively driving the ultrasound transducer at the set rotation speed once the temporary sensing window has ended, as indicated at block 646. For example, in some cases, a sensing window may have a duration that ranges from 30 microseconds to over 200 microseconds and may occur with a frequency that ranges from 4 kHz to 33 kHz.

Figure 10:
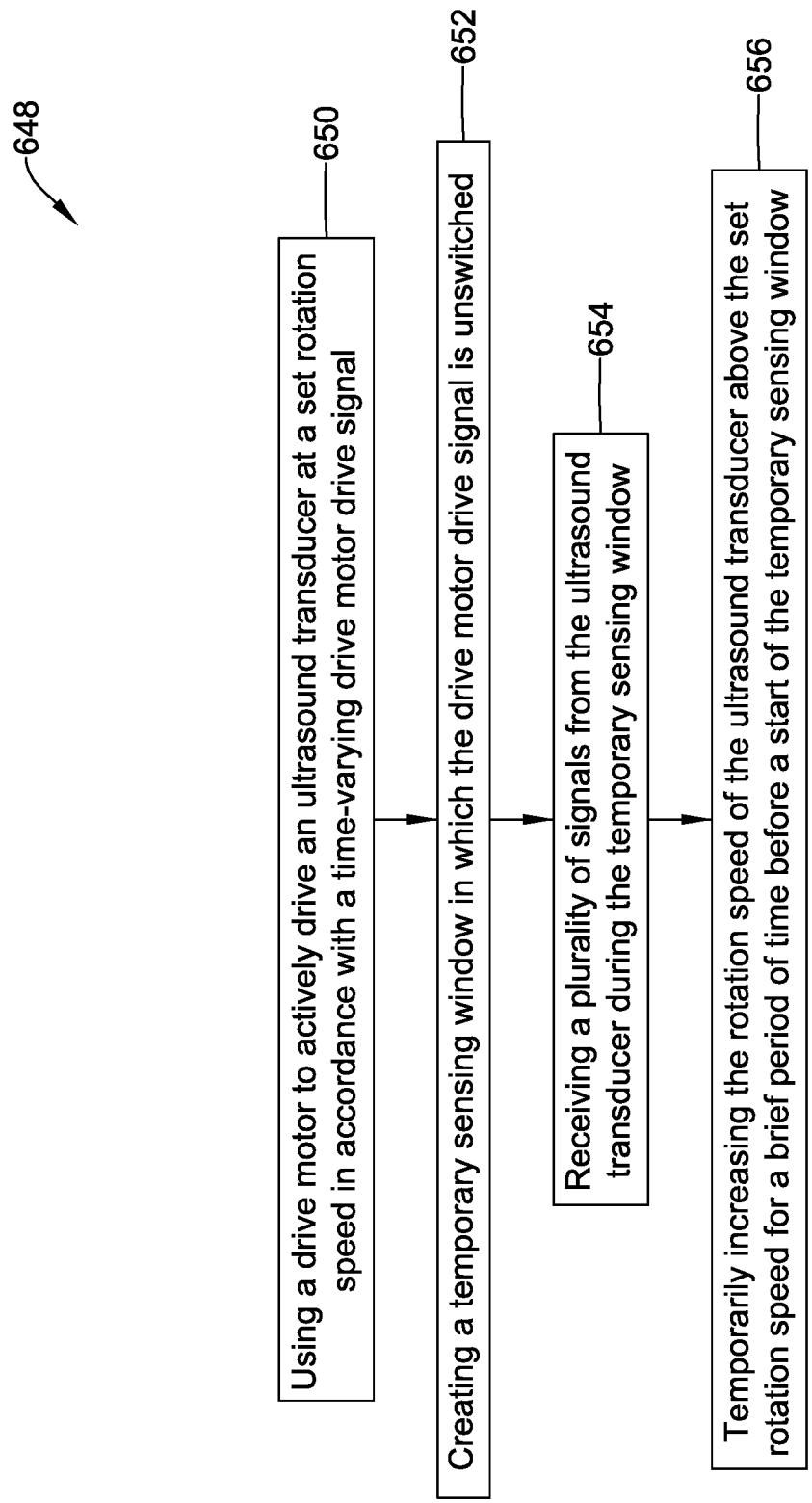
FIG. 10 is a flow diagram showing an illustrative method of capturing intravascular ultrasound images.

FIG. 10 is a flow diagram showing an illustrative method 648 for capturing intravascular ultrasound images. The method 648 includes using a drive motor (such as the drive motor 406) to actively drive an ultrasound transducer (such as the ultrasound transducer 312 or the ultrasound transducer 404) at a set rotation speed in accordance with a time-varying drive motor drive signal, as indicated at block 650. In some cases, the time-varying drive motor signal may include a PWM drive motor signal, for example. The set rotation speed may be set or adjusted by an operator, for example, or may be a factory setting. The set rotation speed represents a target operating speed.

A temporary sensing window is created in which the drive motor drive signal is held constant, i.e., not allowed to vary or switch, as indicated at block 652. In some cases, a sensing window may have a duration that ranges from 30 microseconds to over 200 microseconds and may occur with a frequency that ranges from 4 kHz to 33 kHz. The method 648 includes receiving a plurality of signals from the ultrasound transducer during the temporary sensing window, as indicated at block 654. In some cases, the method 648 may also include temporarily increasing the rotation speed of the ultrasound transducer above the set rotation speed for a brief period of time before a start of the temporary sensing window, as indicated at block 656.

Figure 11:
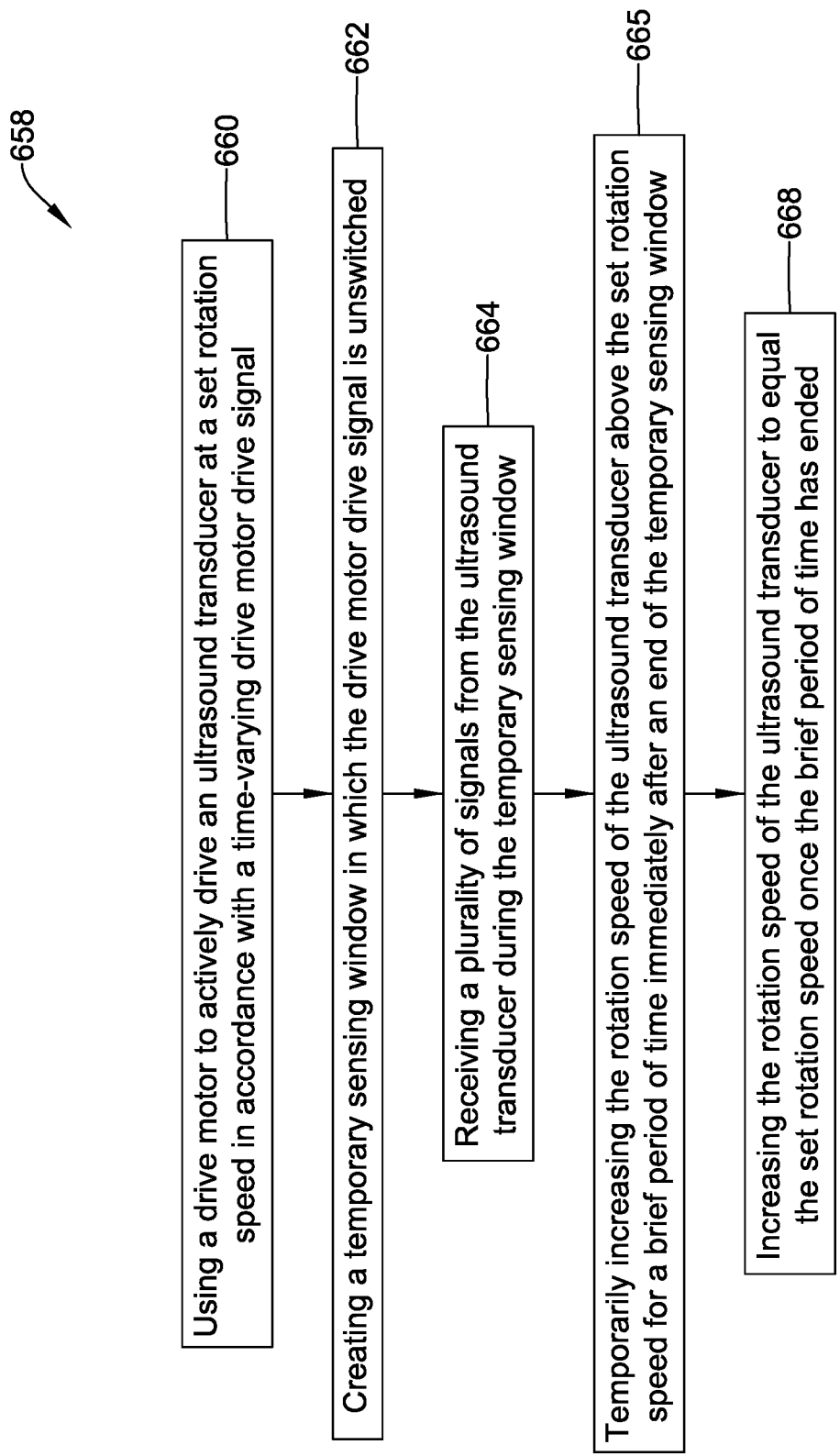
FIG. 11 is a flow diagram showing an illustrative method of capturing intravascular ultrasound images.

FIG. 11 is a flow diagram showing an illustrative method 658 capturing intravascular ultrasound images. The method 658 includes using a drive motor (such as the drive motor 406) to actively drive an ultrasound transducer (such as the ultrasound transducer 312 or the ultrasound transducer 404) at a set rotation speed in accordance with a time-varying drive motor drive signal, as indicated at block 660. In some cases, the time-varying drive motor signal may include a PWM drive motor signal, for example. The set rotation speed may be set or adjusted by an operator, for example, or may be a factory setting. The set rotation speed represents a target operating speed.

A temporary sensing window is created in which the drive motor drive signal is held constant, i.e., not allowed to vary or switch, as indicated at block 662. In some cases, a sensing window may have a duration that ranges from 30 microseconds to over 200 microseconds and may occur with a frequency that ranges from 4 kHz to 33 kHz. The method 658 includes receiving a plurality of signals from the ultrasound transducer during the temporary sensing window, as indicated at block 664.

In some cases, the method 658 may further include temporarily decreasing the rotation speed of the ultrasound transducer, below the set rotation speed, for a brief period of time immediately after an end of the temporary sensing window, as indicated at block 665. The method 658 may further include, for example, increasing the rotation speed of the ultrasound transducer to equal the set rotation speed once the brief period of time has ended, as indicated at block 668. The brief period of time may extend for a duration of near zero up to the entire time period between sampling windows. The time period may vary dynamically depending on motor speed and load.

Figure 12:
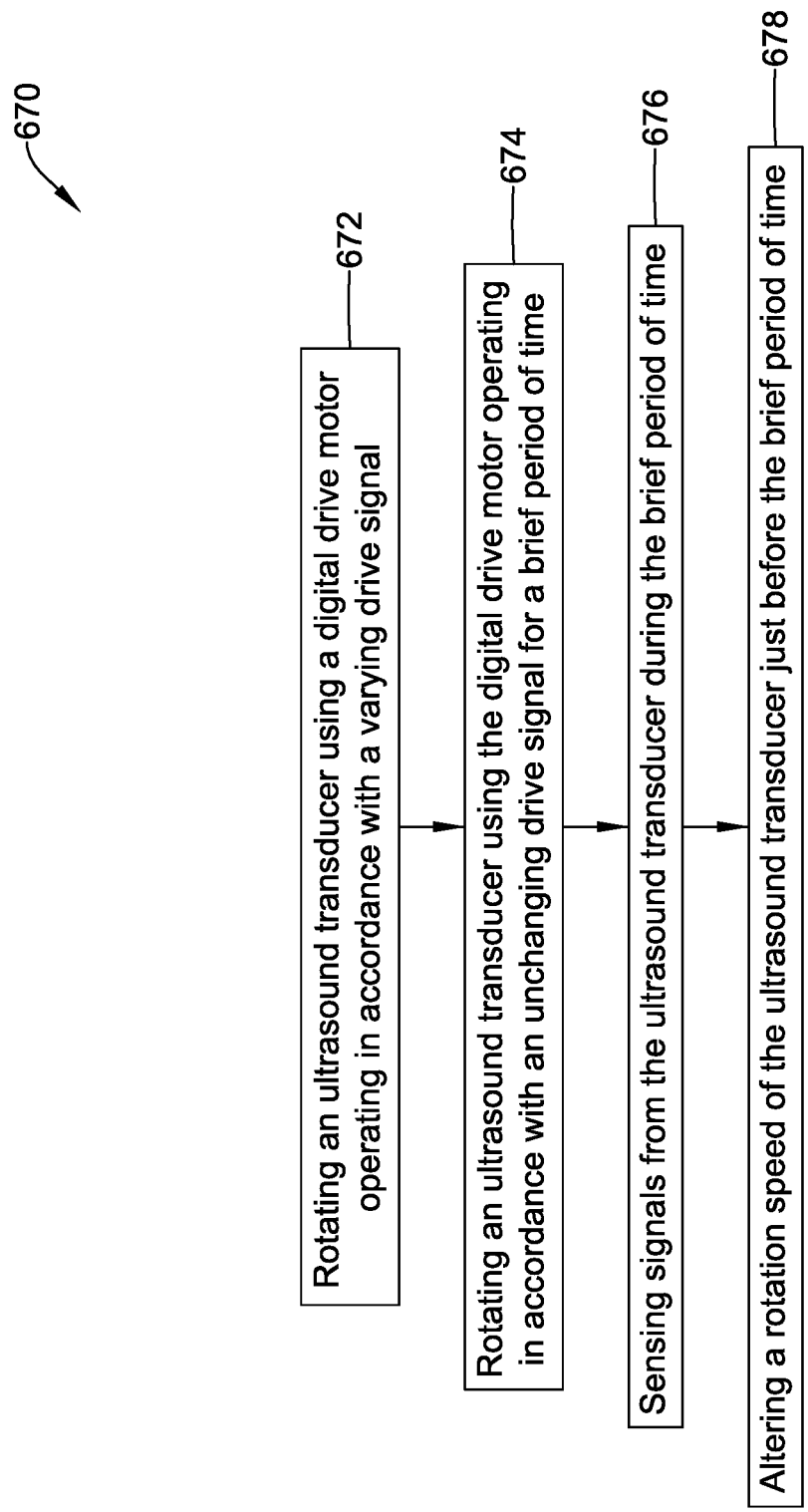
FIG. 12 is a flow diagram showing an illustrative method of capturing intravascular ultrasound images.

FIG. 12 is a flow diagram showing an illustrative method 670 for capturing intravascular ultrasound images. The method 670 includes rotating an ultrasound transducer (such as the ultrasound transducer 312 or the ultrasound transducer 404) using a digital drive motor (such as the drive motor 406) that is operating in accordance with a time-varying drive motor drive signal, as indicated at block 672. In some cases, the time-varying drive motor signal may include a PWM drive motor signal, for example. The set rotation speed may be set or adjusted by an operator, for example, or may be a factory setting. The set rotation speed represents a target operating speed.

The ultrasound transducer is rotated using the digital drive motor operating in accordance with a constant drive signal for a brief period of time, as indicated at block 674. The brief period of time, which may for example represent a sensing window may have a duration that ranges from 30 microseconds to over 200 microseconds and may occur with a frequency that ranges from 4 kHz to 33 kHz. The method 670 includes sensing signals from the ultrasound transducer during the brief period of time, as indicated at block 676. In some cases, sensing signals from the ultrasound transducer may further include not sensing signals form the ultrasound transducer when the ultrasound transducer is being actively driven by a time-varying drive signal. In some cases, the method 670 may further include altering a rotation speed of the ultrasound transducer either just before or just after the brief period of time, as indicated at block 678.

Figure 13:
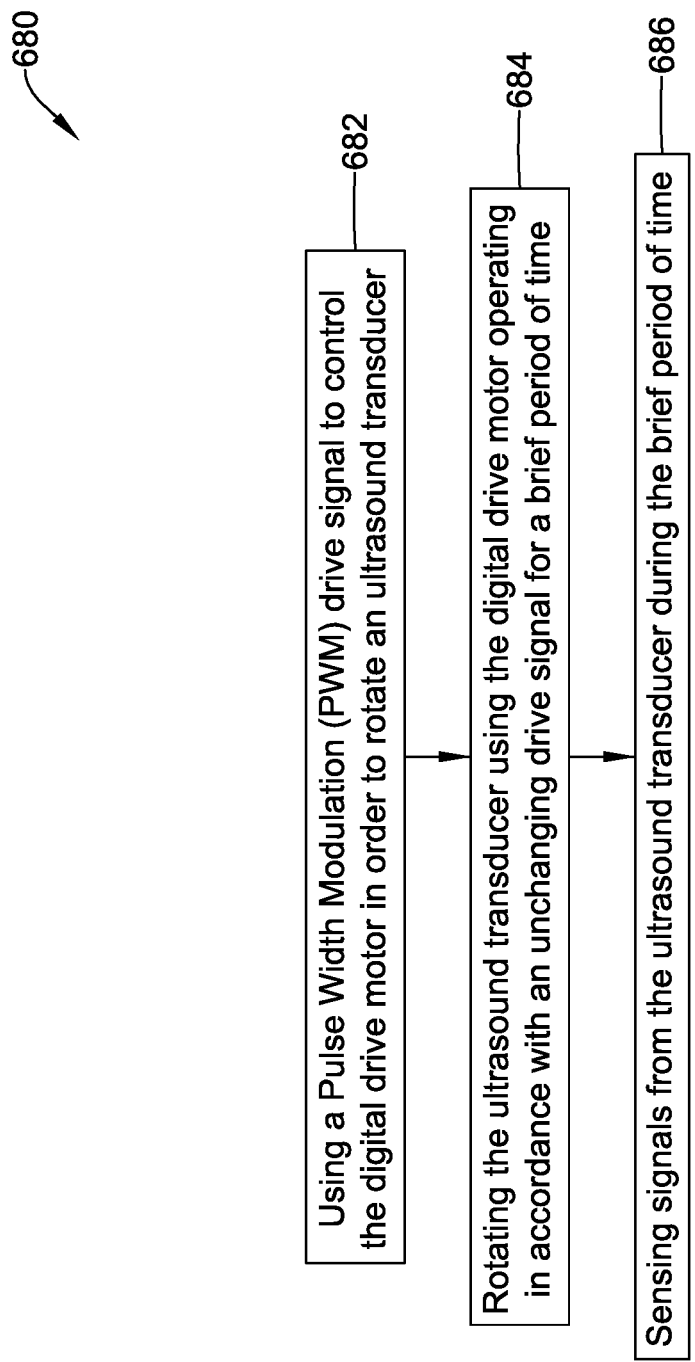
FIG. 13 is a flow diagram showing an illustrative method of capturing intravascular ultrasound images.

FIG. 13 is a flow diagram showing an illustrative method 680 for capturing intravascular ultrasound images. The method 680 includes rotating an ultrasound transducer (such as the ultrasound transducer 312 or the ultrasound transducer 404) using a PWM drive signal in order to control the digital drive motor (such as the drive motor 406), as indicated at block 682. The set rotation speed may be set or adjusted by an operator, for example, or may be a factory setting. The set rotation speed represents a target operating speed.

The ultrasound transducer is rotated using the digital drive motor operating in accordance with a constant drive signal for a brief period of time, as indicated at block 684. The brief period of time, which may for example represent a sensing window, and may have a duration that ranges from 30 microseconds to over 200 microseconds and may occur with a frequency that ranges from 4 kHz to 33 kHz. The method 680 includes sensing signals from the ultrasound transducer during the brief period of time, as indicated at block 686.

Figure 14:
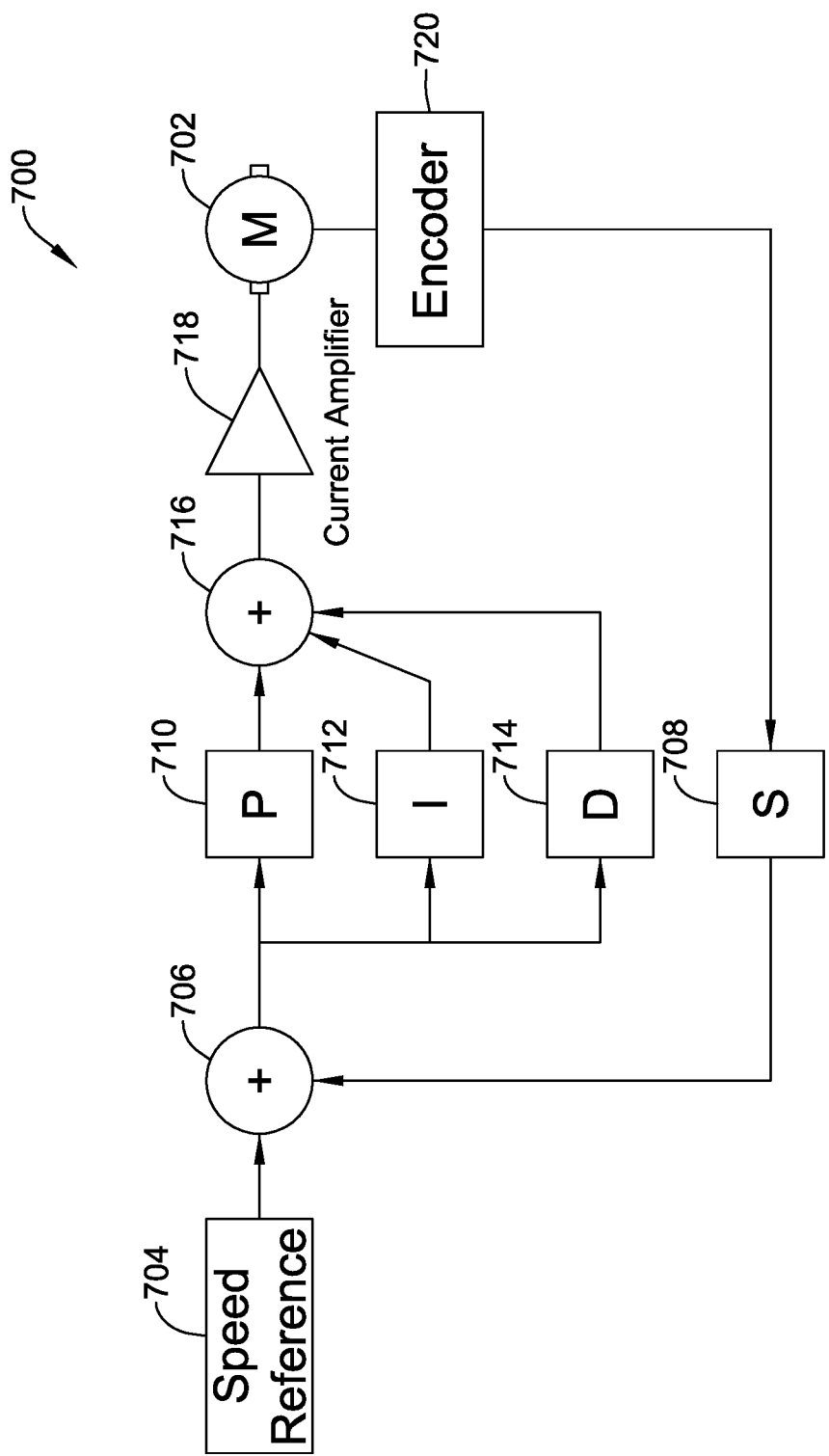
FIG. 14 is a schematic view of an illustrative control algorithm.

FIG. 14 is a schematic view of an illustrative control algorithm 700. The illustrative control algorithm 700 may, for example, be implemented via the processor 106 (FIG. 1) in controlling operation of a drive motor 702 that rotates the ultrasound transducer(s). The control algorithm 700 may be considered as being a PID (Proportional Integral Derivative) control algorithm, although in some cases one or more of the Proportional (P) term, the Integral (I) term and the Derivative (D) term may be set equal to zero. As shown, the Derivative (D) term has been set equal to zero, meaning that the control algorithm 700 essentially represents a PI (Proportional Integral) control algorithm.

A speed reference 704 is provided to a summation point 706, as is a feedback term 708 to produce an error signal. After passing through a Proportional (P) term 710, an Integral (I) term 712 and optionally a Derivative (D) term 714, the signal passes to another summation point 716. After passing through a current amplifier 718, the drive signal reaches the drive motor 702. The state from the drive motor 706 is measured such as via an encoder 720.

Figure 15:
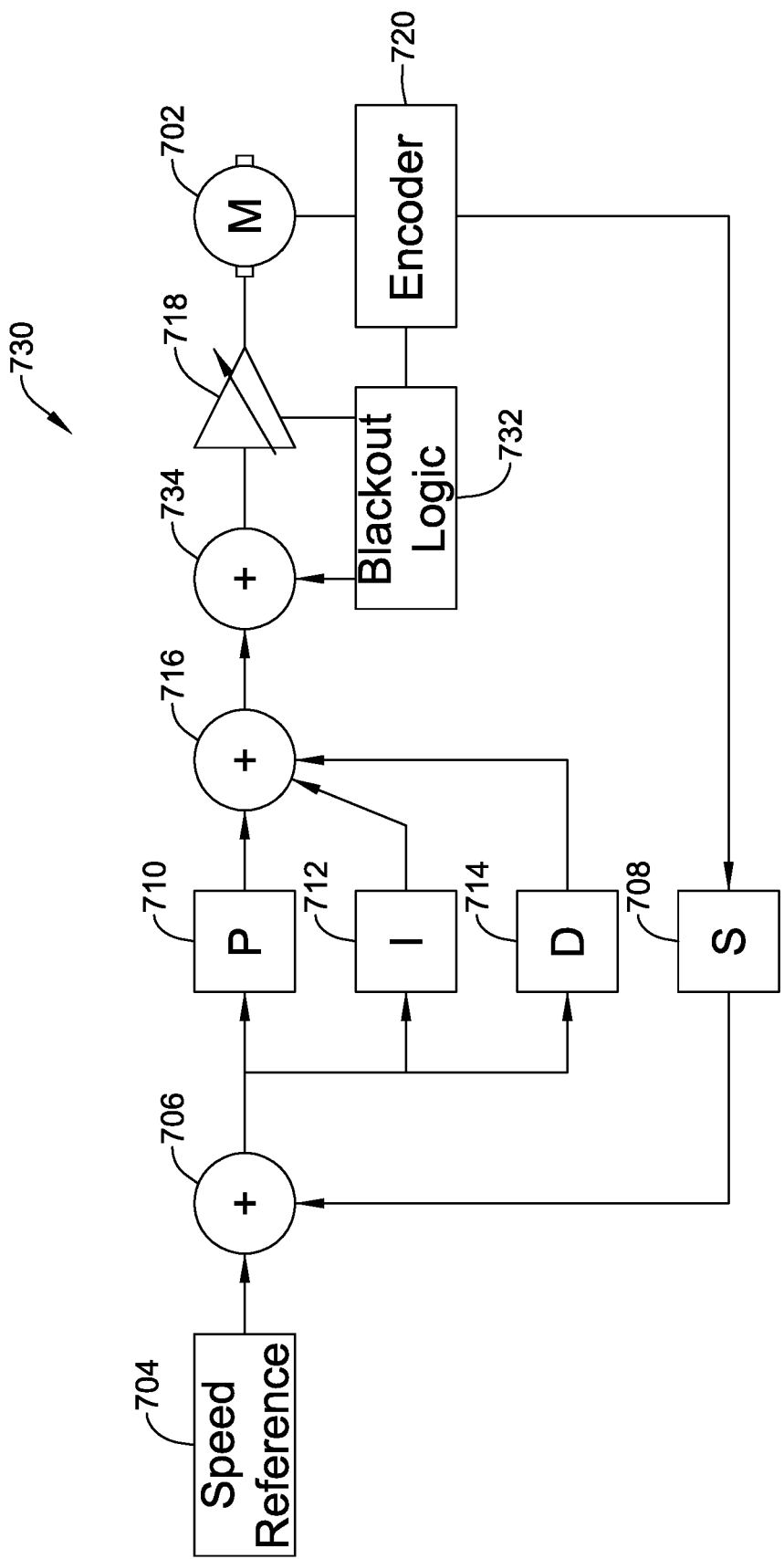
FIG. 15 is a schematic view of an illustrative control algorithm.

FIG. 15 is a schematic view of an illustrative control algorithm 730 that is similar to the control algorithm 730, but includes several additional logical components. The additional logic components include a blackout logic block 732 and an additional summation point 734. The current amplifier 718 is modified such that its state may be forced to an on state or an off state regardless of the incoming drive signal. In some cases, the blackout logic block 732 serves to help modify a time-varying drive motor drive signal, such as but not limited to a PWM drive motor drive signal, in order to provide sensing windows for obtaining signals from the ultrasound transducer without any manifestations of electronic noise otherwise caused by the PWM drive signal changing while attempting to obtain signals.

For example, the blackout logic block 732 may take into account the current state of the PWM drive signal just before a sensing window in order to determine whether the PWM drive signal will be constrained to remain at high, or on, during the sensing window or whether the PWM drive signal will be constrained to remain at low, or off, during the sensing window. If the PWM drive signal will be constrained to remain at high, or on, during the sensing window, meaning that the ultrasound transducer will likely speed up during the sensing window, the blackout logic block 732 may decide to reduce the speed before reaching the sensing window. If the PWM drive signal will be constrained to remain at low, or off, during the sensing window, meaning that the ultrasound transducer will likely slow down during the sensing window, the blackout logic block 732 may decide to increase the speed before reaching the sensing window, and/or to decrease the driven speed for when the sensing window terminates. These are just examples.

Figure 16:
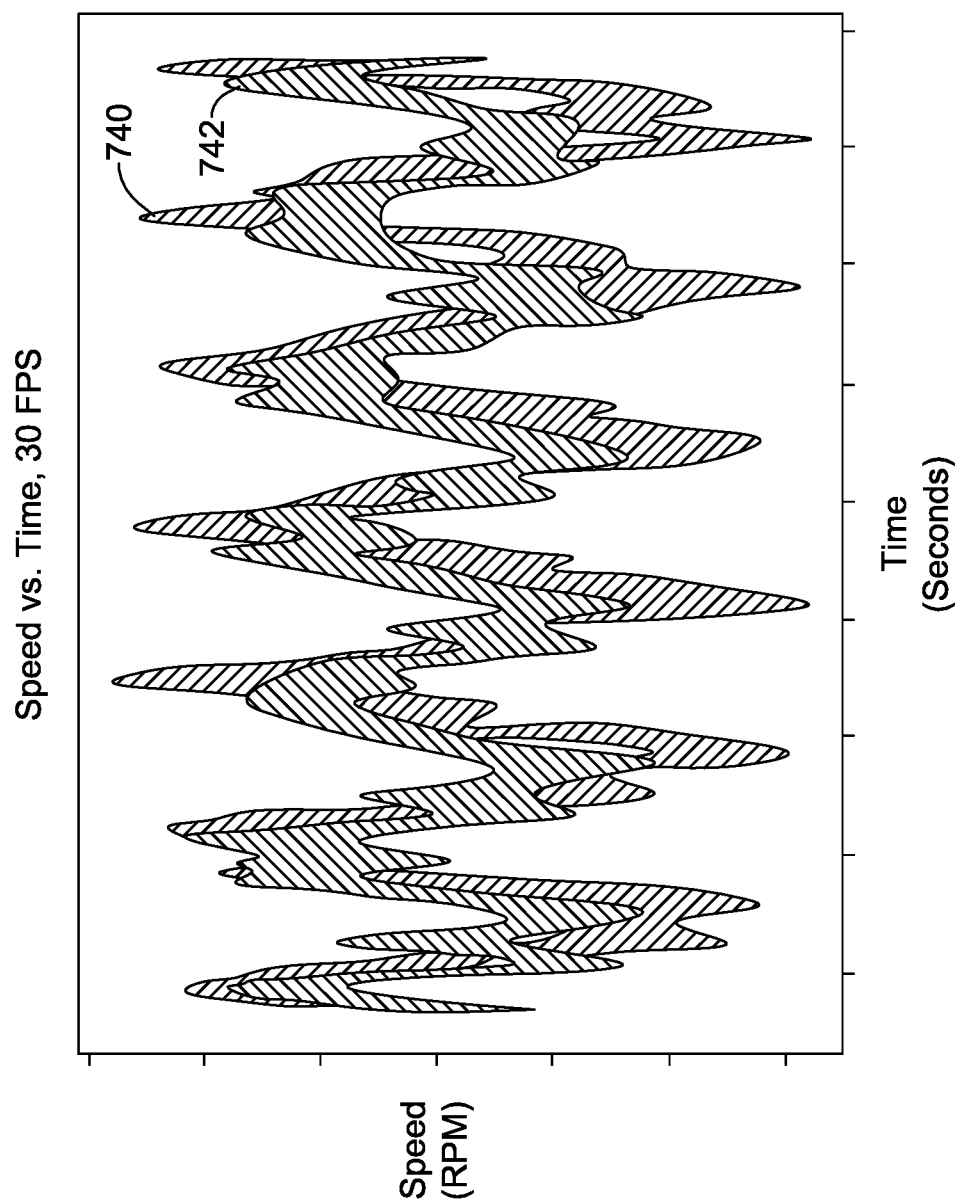
FIG. 16 is a graphical representation of rotation speed versus time data.

FIG. 16 is a graphical representation of speed versus time, where the vertical axis represents rotational speed, in revolutions per minute (RPM) and the horizontal axis represents time in seconds. A first plotted line 740 represents speed versus time performance for a particular ultrasound transducer that is being rotated by an analog motor at a speed that corresponds to 30 frames per second (FPS). A second plotted line 742 represents speed versus time performance for a particular ultrasound transducer that is being rotated by a PWM-controlled drive motor at the same speed. In the case of the PWM-controlled drive motor, the drive motor is being controlled in accordance with periodic sensing windows in which the PWM drive signal is held constant and is not allowed to vary during the sensing windows. As can be seen, the performance of the PWM-controlled motor largely exceeds that of the analog system since the variation in speed is lower.

Figure 17:
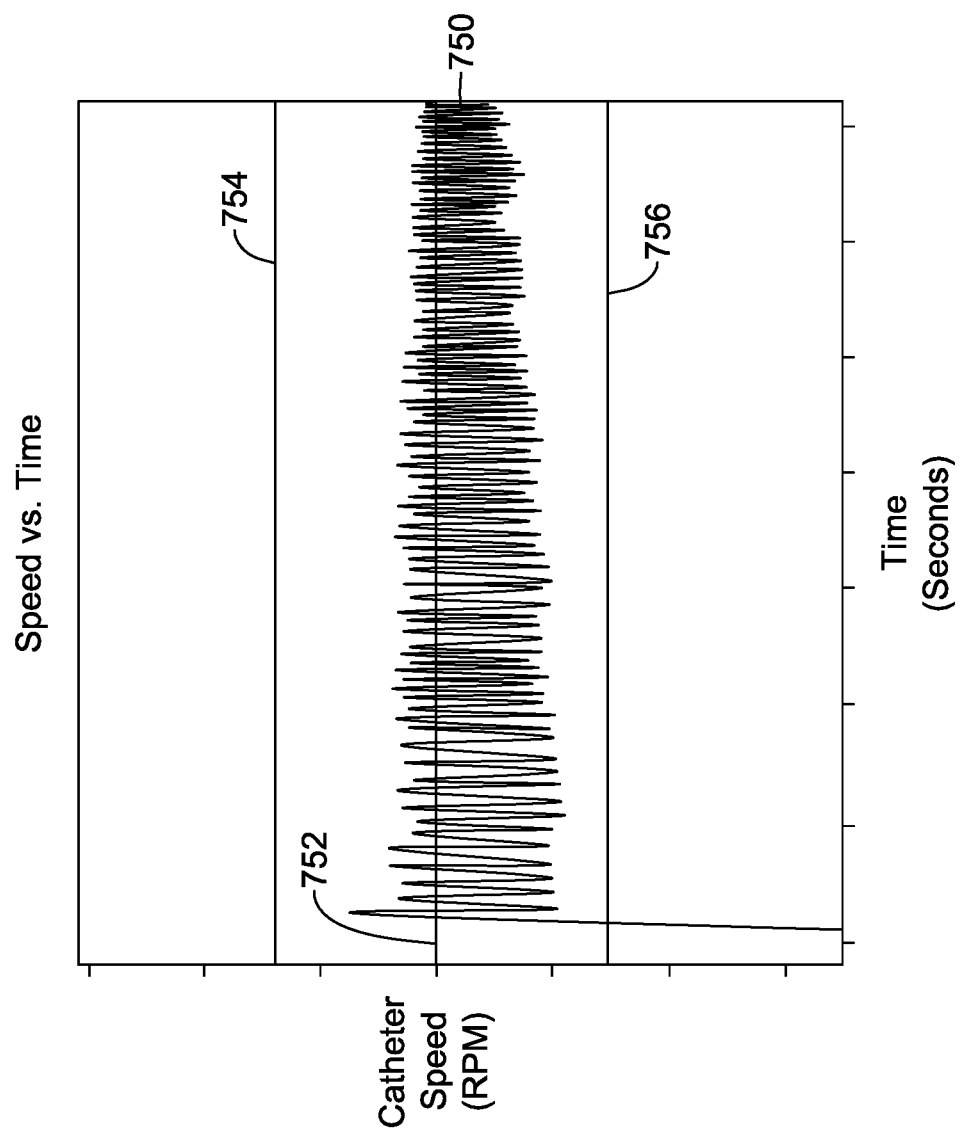
FIG. 17 is a graphical representation of rotation speed versus time data.

FIG. 17 is a graphical representation of speed versus time, where the vertical axis represents rotational speed, in revolutions per minute (RPM) and the horizontal axis represents time in seconds. A first plot line 750 represents speed versus time performance for a particular ultrasound transducer that is being rotated by a PWM-controlled drive motor at speed corresponding to about 30 FPS, relative to a speed reference represented by a plot line 752. A plot line 754 represents a threshold that is set equal to the speed reference plus 1.5 percent while a plot line 756 represents a threshold that is set equal to the speed reference minus 1.5 percent. As can be seen, the use of PWM motor control, in combination with the use of sensing windows, helps to stabilize low-frequency oscillations, and pushes any remaining instabilities up to very high frequencies where they are not an issues. Overall, this shows that the use of PWM motor control provides tight control.

Figure 18:
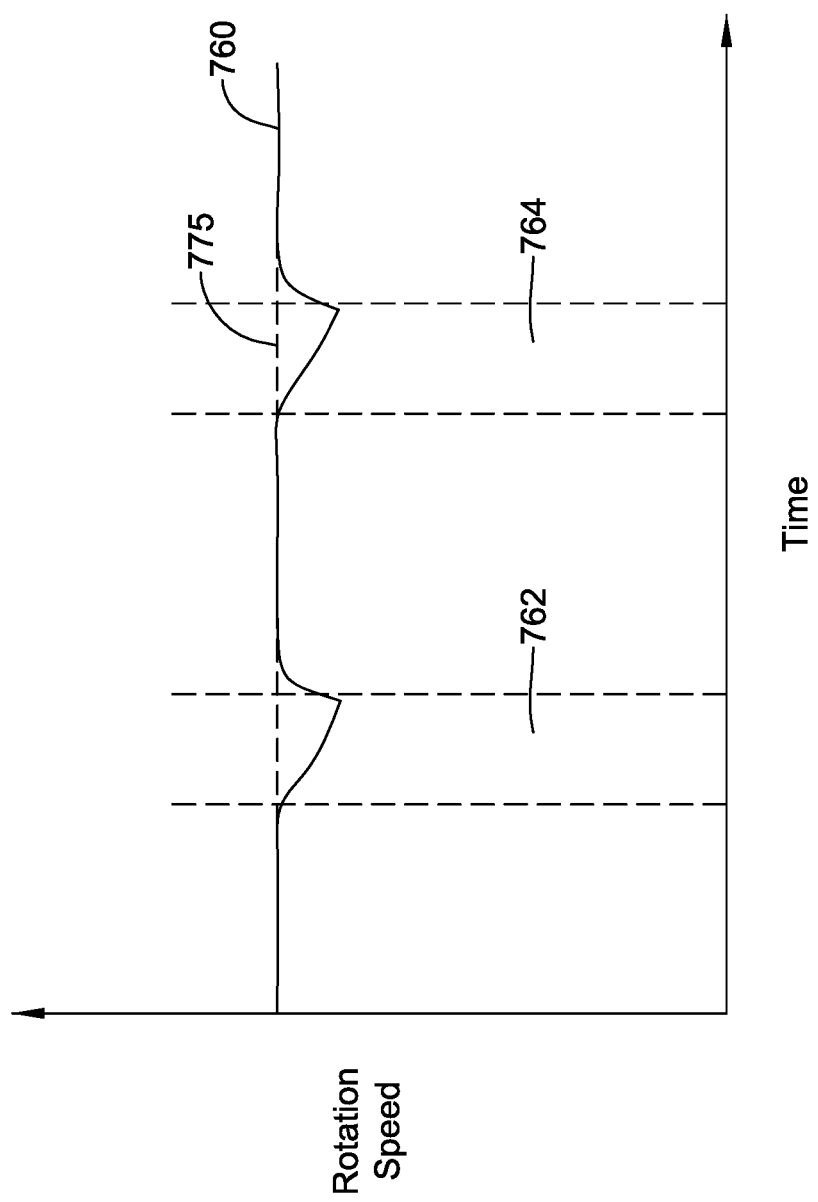
FIG. 18 is a schematic representation of rotation speed versus time.

FIG. 18 is a graphical representation of speed versus time, providing an example of how the rotation speed may vary during sensing windows. As seen in FIG. 18, a plot line 760 shows the rotation speed over time and a plot line 775 shows an illustrative set rotation speed. The rotation speed drops during a sensing window 762 relative to the set rotation speed 775. This represents what may happen when the PWM motor drive signal is constrained to remain low, or off, during the sensing window 762. The rotation speed returns to the set rotation speed 775 prior to the sensing window 762 a short period of time after the sensing window 762 terminates. The rotation speed drops during a sensing window 764. Again, this represents what may happen when the PWM motor drive signal is constrained to remain low, or off, during the sensing window 764. If the PWM motor drive signal was instead constrained to remain high, or on, during the sensing window 762 and/or the sensing window 764, it will be appreciated that the rotation speed would instead increase during the sensing windows 762 and 764, respectively.

Figure 19:
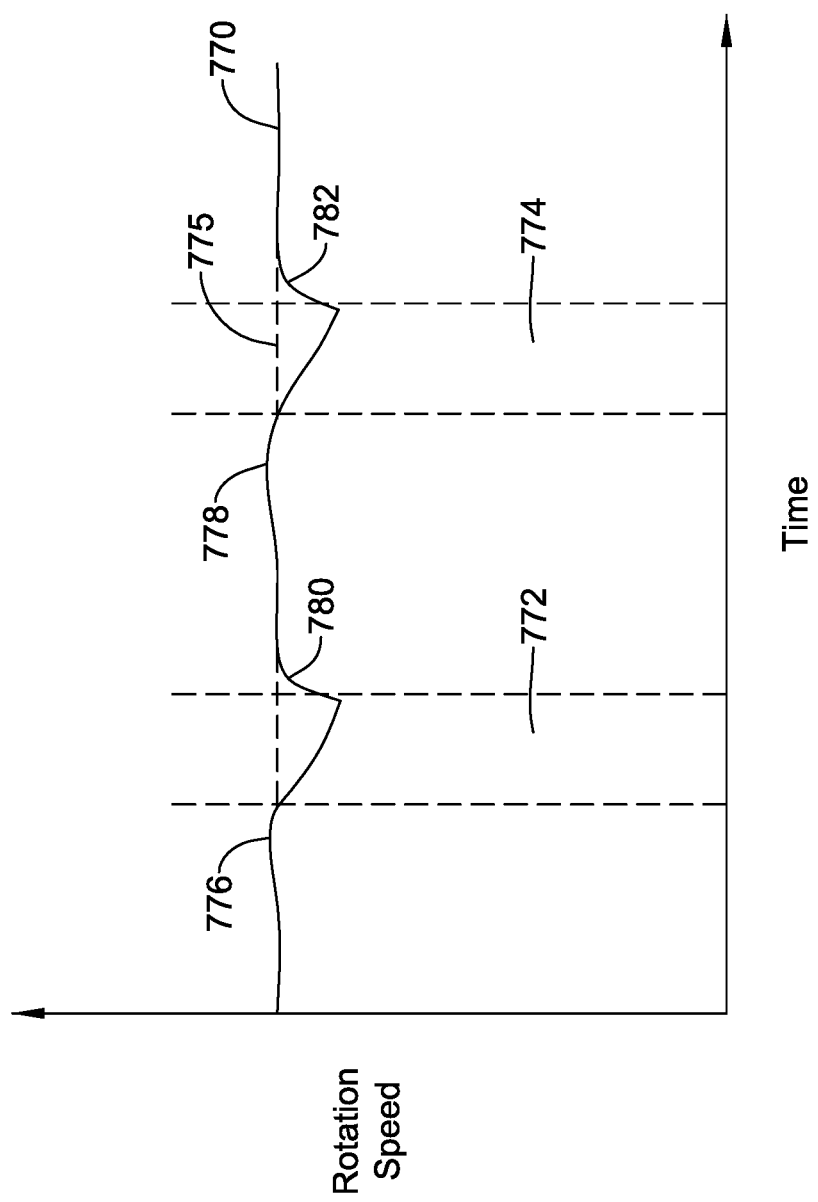
FIG. 19 is a schematic representation of rotation speed versus time.

FIG. 19 is a graphical representation of speed versus time, providing an example of how the rotation speed may vary during sensing windows. As seen in FIG. 19, a plot line 770 shows the rotation speed over time and the plot line 775 shows an illustrative set rotation speed. FIG. 19 shows a first sensing window 772 and a second sensing window 774. Moving left to right, it can be seen that the rotation speed as shown in the plot line 770 increases just before the first sensing window 772. This bump 776 in the plot line 770 represents an increase in rotation speed that may, for example, be commanded in response to various size parameters of the ultrasound catheter and/or when the PWM drive signal will be constrained to off, or low, during the first sensing window 772.

The rotation speed as shown in the plot line 770 decreases during the first sensing window 772. In some cases, coming out of the first sensing window 772, the rotation speed may be commanded to return to a rotation speed that is less than what it was before, as indicated by a curve 780. Similarly, the rotation speed as shown in the plot line 770 increases just before the second sensing window 774. This bump 778 in the plot line 770 represents an increase in rotation speed that may, for example, be commanded in response to various size parameters of the ultrasound catheter and/or when the PWM drive signal will be constrained to off, or low, during the second sensing window 774. In some cases, coming out of the second sensing window 774, the rotation speed may be commanded to return to a rotation speed that is less than a set rotation speed The processes and/or display output may be used to extract clinically relevant IVUS features, guide treatment strategies such as calcium management, present intuitive maps, and/or combine information on a single display unit or set of display units.

Some example IVUS imaging systems that may be used, for example with the methods disclosed herein, include, but are not limited to, those disclosed in, for example, U.S. Pat. Nos. 7,246,959; 7,306,561; and 6,945,938; as well as U.S. Patent Application Publication Nos. US 2006/0100522; US 2006/0106320; US 2006/0173350; US 2006/0253028; US 2007/0016054; and US 2007/0038111; all of which are incorporated herein by reference.

U.S. Patent Application Publication No. US 2015/0073279 is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method for capturing intravascular ultrasound images using a mechanically steered transducer, the method comprising:
   generating an electronic Pulse Width Modulation (PWM) drive signal;
   using the electronic PWM drive signal that switches between high and low states in normal operation in order to actuate an electric drive motor for an intravascular ultrasound catheter including an ultrasound transducer in order to rotate the ultrasound transducer at a set rotation speed;
   creating an electrical noise reduction sensing window by temporarily maintaining the electronic PWM drive signal in a constant state without switching between high and low states to prevent electrical interference with ultrasound sensing; and
   receiving a plurality of signals from the ultrasound transducer during the electrical noise reduction sensing window while the electronic PWM drive signal remains in the constant state.

2. The method of claim 1, further comprising resuming normal operation by allowing the electronic PWM drive signal to switch between high and low states after the electrical noise reduction sensing window has terminated.

3. The method of claim 1, further comprising altering the electronic PWM drive signal in order to adjust a rotation speed of the ultrasound transducer relative to the set rotation speed before a start of the electrical noise reduction sensing window.

4. The method of claim 3, wherein altering the electronic PWM drive signal in order to adjust a rotation speed of the ultrasound transducer comprises altering the electronic PWM drive signal in order to rotate the ultrasound transducer at an increased rotation speed greater than the set rotation speed before the start of the electrical noise reduction sensing window.

5. The method of claim 4, wherein the increased rotation speed lasts for a first period of time terminating at the start of the electrical noise reduction sensing window.

6. The method of claim 1, further comprising altering the electronic PWM drive signal in order to adjust a rotation speed of the ultrasound transducer relative to the set rotation speed after an end of the electrical noise reduction sensing window.

7. The method of claim 6, wherein altering the electronic PWM drive signal in order to adjust a rotation speed of the ultrasound transducer comprises altering the electronic PWM drive signal in order to rotate the ultrasound transducer at a decreased speed relative to the set rotation speed after the end of the electrical noise reduction sensing window.

8. The method of claim 7, further comprising altering the electronic PWM drive signal in order to return to rotating the ultrasound transducer at the set rotation speed after a second period of time beginning at the end of the electrical noise reduction sensing window.

9. A method for capturing intravascular ultrasound images using a catheter, the method comprising:
   using a drive motor located in a control module proximal to the catheter to actively drive an ultrasound transducer located in a distal region of the catheter at a set rotation speed in accordance with a time-varying drive motor drive signal;
   creating a temporary sensing window in which the drive motor drive signal is unswitched between high and low states; and
   receiving a plurality of signals from the ultrasound transducer during the temporary sensing window.

10. The method of claim 9, further comprising reverting to allowing the drive motor drive signal to be switched between high and low states in order to drive the ultrasound transducer at the set rotation speed once the temporary sensing window has ended.

11. The method of claim 9, further comprising temporarily increasing the rotation speed of the ultrasound transducer above the set rotation speed before a start of the temporary sensing window.

12. The method of claim 9, further comprising temporarily decreasing the rotation speed of the ultrasound transducer, below the set rotation speed, after an end of the temporary sensing window.

13. The method of claim 12, further comprising subsequently increasing the rotation speed of the ultrasound transducer to equal the set rotation speed.

14. The method of claim 9, wherein the drive motor is controlled via a Pulse Width Modulation (PWM) drive signal.

15. The method of claim 9, wherein a state of the drive motor drive signal during the temporary sensing window is dynamically determined based on motor speed and/or load.

16. A method for capturing intravascular ultrasound images, the method comprising:
   rotating an ultrasound transducer using a digital drive motor operating in accordance with a varying drive signal that switches between high and low states;
   rotating the ultrasound transducer using the digital drive motor operating in accordance with an unchanging drive signal that does not switch between high and low states for a brief period of time;
   not sensing signals from the ultrasound transducer when the digital drive motor is operating in accordance with the varying drive signal; and
   sensing signals from the ultrasound transducer during the brief period of time.

17. The method of claim 16, wherein a state of the drive motor drive signal during the temporary sensing window is dynamically determined based on motor speed and/or load.

18. The method of claim 17, further comprising using a Pulse Width Modulation (PWM) drive signal to control the digital drive motor.

19. The method of claim 18, further comprising altering a rotation speed of the ultrasound transducer either just before or just after the brief period of time.

* * * * *